US011529618B2

(12) United States Patent
McGuire et al.

(10) Patent No.: US 11,529,618 B2
(45) Date of Patent: Dec. 20, 2022

(54) CATALYST COMPOSITE COMPRISING AN ALKALINE EARTH METAL CONTAINING CHA ZEOLITE AND USE THEREOF IN A PROCESS FOR THE CONVERSION OF OXYGENATES TO OLEFINS

(71) Applicant: BASF SE, Ludwigshafen am Rhein (DE)

(72) Inventors: Robert McGuire, Florham Park, NJ (US); Christiane Janke, Ludwigshafen am Rhein (DE); Ulrich Mueller, Ludwigshafen am Rhein (DE); Ekkehard Schwab, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 31 days.

(21) Appl. No.: 16/462,408

(22) PCT Filed: Nov. 28, 2017

(86) PCT No.: PCT/EP2017/080654
§ 371 (c)(1),
(2) Date: May 20, 2019

(87) PCT Pub. No.: WO2018/096171
PCT Pub. Date: May 31, 2018

(65) Prior Publication Data
US 2019/0366313 A1 Dec. 5, 2019

(30) Foreign Application Priority Data

Nov. 28, 2016 (EP) .................................... 16200871

(51) Int. Cl.
B01J 29/70 (2006.01)
C07C 1/20 (2006.01)
C10G 3/00 (2006.01)
C10G 11/18 (2006.01)
B01J 29/04 (2006.01)
(Continued)

(52) U.S. Cl.
CPC ......... B01J 29/7015 (2013.01); B01J 29/047 (2013.01); B01J 29/7065 (2013.01); B01J 29/783 (2013.01); B01J 29/86 (2013.01); B01J 29/87 (2013.01); B01J 29/89 (2013.01); C07C 1/20 (2013.01); C10G 3/44 (2013.01); C10G 11/18 (2013.01); B01J 35/0006 (2013.01); B01J 37/0009 (2013.01); B01J 37/0201 (2013.01); B01J 2229/186 (2013.01); B01J 2229/20 (2013.01); B01J 2229/42 (2013.01); C07C 11/04 (2013.01); C07C 11/08 (2013.01); C07C 2529/70 (2013.01); C07C 2529/78 (2013.01); C07C 2529/85 (2013.01);
(Continued)

(58) Field of Classification Search
CPC .. B01J 29/7015; B01J 29/7065; B01J 29/047; B01J 29/783; B01J 29/86; B01J 29/87; B01J 29/89; B01J 2229/18; B01J 2229/186; B01J 2229/20; B01J 2229/42; B01J 37/0201; B01J 37/0009; B01J 35/0006; C07C 2529/89; C07C 2529/87; C07C 2529/86; C07C 2529/78; C07C 2529/70; C07C 1/20; C07C 11/04; C07C 11/08; Y02P 20/52; Y02P 30/20; Y02P 30/40; C10G 11/18; C10G 3/44
USPC ...... 502/60, 61, 63, 64, 65, 69, 73; 585/446, 585/638, 639, 640
See application file for complete search history.

(56) References Cited
U.S. PATENT DOCUMENTS 4,544,538 A * 10/1985 Zones ..................... B01J 29/70
423/706
4,925,460 A * 5/1990 Coe ......................... B01D 53/02
502/60
(Continued)

FOREIGN PATENT DOCUMENTS

CN 1441701 A 9/2003
EP 418142 A1 3/1991
(Continued)

OTHER PUBLICATIONS

U.S. Appl. No. 16/310,645, filed Dec. 17, 2018, Parvulescu et al.
(Continued)

Primary Examiner — Elizabeth D Wood
(74) Attorney, Agent, or Firm — Faegre Drinker Biddle & Reath LLP

(57) ABSTRACT

The present invention relates to catalyst comprising one or more metal oxides and/or metalloid oxides and a zeolitic material having the CHA framework structure comprising $YO_2$ and $X_2O_3$, wherein Y is a tetravalent element and X is a trivalent element, wherein the zeolitic material comprises one or more alkaline earth metals selected from the group consisting of Mg, Ca, Sr, Ba, and combinations of two or more thereof, and wherein the framework of the zeolitic material comprised in the catalyst contains substantially no phosphorous, as well as to a process for the preparation of a catalyst comprising one or more alkaline earth metals selected from the group consisting of Mg, Ca, Sr, Ba, and combinations of two or more thereof and to a catalyst obtainable therefrom. Furthermore, the present invention relates to a method for the conversion of oxygenates to olefins employing the inventive catalyst, as well as to the use of the inventive catalyst in specific applications.

19 Claims, 5 Drawing Sheets

(51) Int. Cl.
*B01J 29/87* (2006.01)
*B01J 29/89* (2006.01)
*B01J 29/78* (2006.01)
*B01J 29/86* (2006.01)
*C07C 11/04* (2006.01)
*C07C 11/08* (2006.01)
*B01J 37/02* (2006.01)
*B01J 35/00* (2006.01)
*B01J 37/00* (2006.01)

(52) U.S. Cl.
CPC ...... *C07C 2529/86* (2013.01); *C07C 2529/87* (2013.01); *C07C 2529/89* (2013.01)

(56) References Cited

U.S. PATENT DOCUMENTS

| | | |
|---|---|---|
| 5,095,163 A | 3/1992 | Barger |
| 5,126,308 A | 6/1992 | Barger et al. |
| 5,182,242 A * | 1/1993 | Marler ............... B01J 29/40 502/66 |
| 5,430,000 A * | 7/1995 | Timken ............... B01J 29/40 502/60 |
| 5,912,393 A | 6/1999 | Barger et al. |
| 5,925,586 A | 7/1999 | Sun |
| 5,932,512 A | 8/1999 | Sun |
| 5,962,762 A | 10/1999 | Sun et al. |
| 6,005,155 A | 12/1999 | Sun |
| 6,040,264 A | 3/2000 | Sun et al. |
| 6,046,371 A | 4/2000 | Wu et al. |
| 6,051,745 A | 4/2000 | Wu et al. |
| 6,051,746 A | 4/2000 | Sun et al. |
| 6,448,197 B1 | 9/2002 | Liu et al. |
| 6,576,120 B1 * | 6/2003 | Van Ballegoy ........ B01J 29/06 208/108 |
| 6,825,391 B2 | 11/2004 | Janssen et al. |
| 7,078,364 B2 | 7/2006 | Haw et al. |
| 7,999,962 B2 * | 8/2011 | Yasuzaki ............ H04N 1/00912 358/1.15 |
| 8,148,587 B2 | 4/2012 | Qi et al. |
| 8,961,914 B2 * | 2/2015 | Mohanan ............ B01J 37/0246 423/213.2 |
| 2004/0048734 A1 | 3/2004 | Liu et al. |
| 2016/0101415 A1 | 4/2016 | Ji et al. |
| 2017/0362513 A1 | 12/2017 | McGuire et al. |
| 2018/0022611 A1 | 1/2018 | Feyen et al. |
| 2018/0036723 A1 | 2/2018 | Riedel et al. |
| 2018/0085739 A1 | 3/2018 | Milanov et al. |
| 2018/0170850 A1 | 6/2018 | Vautravers et al. |
| 2018/0208532 A1 | 7/2018 | Parvulescu et al. |
| 2018/0243691 A1 | 8/2018 | Mueller et al. |
| 2018/0328601 A1 | 11/2018 | Weickert et al. |
| 2018/0333696 A1 | 11/2018 | Burckhart et al. |
| 2018/0345245 A1 | 12/2018 | Maurer et al. |
| 2018/0362351 A1 | 12/2018 | Parvulescu et al. |
| 2018/0362353 A1 | 12/2018 | Vautravers et al. |
| 2018/0362357 A1 | 12/2018 | Feyen et al. |
| 2019/0077779 A1 | 3/2019 | Riedel et al. |
| 2019/0134564 A1 | 5/2019 | Feyen et al. |
| 2019/0143272 A1 | 5/2019 | Trukhan et al. |
| 2019/0144290 A1 | 5/2019 | Marx et al. |
| 2019/0169037 A1 | 6/2019 | Trukhan et al. |
| 2019/0169149 A1 | 6/2019 | Teles et al. |
| 2019/0210989 A1 | 7/2019 | Teles et al. |

FOREIGN PATENT DOCUMENTS

| | | |
|---|---|---|
| WO | WO-9829370 A1 | 7/1998 |
| WO | WO-0160746 A1 | 8/2001 |
| WO | WO-0162382 A2 | 8/2001 |
| WO | WO-2014062952 A1 | 4/2014 |
| WO | WO/2016116406 | 7/2016 |
| WO | WO-2016116406 A1 | 7/2016 |
| WO | WO/2017211236 | 12/2017 |
| WO | WO-2017211236 A1 | 12/2017 |

OTHER PUBLICATIONS

U.S. Appl. No. 16/315,345, filed Jan. 4, 2019, Teles et al.
U.S. Appl. No. 16/462,408, filed May 20, 2019, McGuire et al.
Applied Catalysis, "Synthesis of Silicoaluminophosphate Zeolite SAPO-34", vol. 40, No. 1-2, (1988), p. 316.
Hasegawa, Y., et al., "Preparation of novel chebazite (CHA)-type zeolite layer on porous $\alpha$-$Al_2O_3$ tube using template-free solution", Journal of Membrane Science, vol. 347, No. 1-2, (2010), pp. 193-196.
International Preliminary Report on Patentability for PCT/EP2017/080654 dated Jan. 29, 2018.
Itakura, M., et al., "Synthesis of high-silica CHA type zeolite by interzeolite conversion of FAU type zeolite in the presence of seed crystals", Microporous and Mesoporous Materials, vol. 144, No. 1-3, (2011), pp. 91-96.
Ji, Y., et al., "Organic-Free Synthesis of CHA-Type Zeolite Catalysts for the Methanol-to-Olefins Reaction", ACS Catalysis, vol. 5, No. 7, (2015), pp. 4456-4465.
Kang, M., et al., "Effects of decrease in number of acid sites located on the external surface of Ni-SAPO-34 crystalline catalyst by the mechanochemical method", Catalysis Letters, vol. 53, No. 3/04, (1998), pp. 171-176.
Liang, J., et al., "Characteristics and Performance of SAPO-34 Catalyst for Methanol-to-Olefin Conversion", Applied Catalysis, vol. 64, (1990), pp. 31-40.
Yarulina, I., et al., "Methanol-to-olefins process over zeolite catalysts with DDR topology: effect of composition and structural defects on catalytic performance", Catalysis Science & Technology, vol. 6, No. 8, (2016), pp. 2663-2678..
Zhang, J., et al., "Alkali and alkaline-earth cation exchanged chabazite zeolites for adsorption based on $CO_2$ capture", Microporous and Mesoporous Materials, vol. 111, Nos. 1-3, (2008), pp. 478-487.
U.S. Appl. No. 16/086,251.
U.S. Appl. No. 16/310,645, filed Dec. 17, 2018.
U.S. Appl. No. 16/315,345, filed Jan. 4, 2019.
U.S. Appl. No. 16/330,592.
U.S. Appl. No. 16/336,661.
U.S. Appl. No. 16/462,408.

* cited by examiner

CATALYST COMPOSITE COMPRISING AN ALKALINE EARTH METAL CONTAINING CHA ZEOLITE AND USE THEREOF IN A PROCESS FOR THE CONVERSION OF OXYGENATES TO OLEFINS

CROSS-REFERENCE TO RELATED APPLICATIONS

This application is a national stage application (under 35 U.S.C. § 371) of PCT/EP2017/080654, filed Nov. 28, 2017, which claims benefit of European Application No. 16200871.8, filed Nov. 28, 2016, both of which are incorporated herein by reference in their entirety.

TECHNICAL FIELD

The present invention relates to a catalyst comprising one or more metal oxides and/or metalloid oxides and a zeolitic material having the CHA framework structure comprising $YO_2$ and $X_2O_3$, wherein Y is a tetravalent element and X is a trivalent element, wherein the zeolitic material comprises one or more alkaline earth metals selected from the group consisting of Mg, Ca, Sr, Ba, and combinations of two or more thereof, and wherein the framework of the zeolitic material comprised in the catalyst contains substantially no phosphorous. Furthermore, the present invention relates to a process for the production of the inventive catalyst and to a process for the conversion of oxygenates to olefins employing the inventive catalyst. Finally, the present invention relates to the use of the inventive catalyst, in particular in the conversion of oxygenates to olefins.

INTRODUCTION

The conversion of oxygenates (methanol, ethanol and dimethyl ether) to olefins has a high technical potential as an alternative, non-petroleum based route for obtaining petrochemical raw materials like for instance the olefins ethylene, propylene and butylenes. Suitable catalysts are zeolite based e.g. ZSM-5 (MFI), ZSM-11 (MEL), and SAPO-34 (CHA), as well as isomorphous zeolites from the pentasil family. The conversion of oxygenates can either proceed in a fluidized or fixed bed reactor—depending on which type of zeolite is used. SAPO-based catalysts have higher selectivities to lower olefins but coke/deactivate rapidly, thus, they are usually used in fludized mode. In contrast, ZSM-5 based catalysts have lower olefin selectivities than SAPO-based catalysts, but deactivation (loss of conversion) in a single-pass reaction cycle is much slower. In both catalysts binders are used to shape the zeolite materials to particles/granulates or extrudates for use in the appropriate reactor type (extrudates: fixed bed; fluidizable particles).

China's Dalian Institute of Chemical Physics (DICP) first demonstrated and reported good performance of SAPO-34 catalyst in MTO reaction (Applied Catalysis 1988, Vol. 40, No. 1-2, p. 316; Applied Catalysis 1990, vol. 64, pp. 31-40, 1990. In DICP's DMTO process, light olefins are selectively produced from methanol, or from dimethyl ether generated from the dehydration of methanol, in the presence of a SAPO-34 molecular sieve catalyst (U.S. Pat. No. 8,148, 587). U.S. Pat. No. 6,448,197, US 20040048734, and CN 1441701A respectively relate to the use of framework-substituted and metal-exchanged forms of SAPO catalysts. Numerous further modifications have been explored such as in WO 0162382 which concerns the use of single ring aromatics as modifying agents including, WO 0160746 the use of surface silica, U.S. Pat. No. 6,005,155 the use of oxygenated chelating agents, U.S. Pat. No. 5,932,512 the use of fluorine, U.S. Pat. No. 6,051,746 the use of polynuclear aromatic heterocyclic compounds, WO 9829370 the use of ytterbium or titanium, U.S. Pat. No. 5,925,586 the use of phosphorus, U.S. Pat. No. 6,040,264 the use of alkaline earth metal, and U.S. Pat. No. 5,962,762 the use of nickel or cobalt. Furthermore, U.S. Pat. Nos. 5,912,393 and 5,126,308 respectively disclose using SAPO-34 molecular sieves with small particle size (less than 1 µm) and reduced silicon content (<0.05 mol %), wherein said combination of properties is claimed to reduce propane by-product formation and increase the catalyst life. U.S. Pat. No. 5,095,163 claims that hydrothermal treatment of SAPO-34 to reduce acidity can also have a beneficial effect on performance. U.S. Pat. No. 6,046,371 describe the use of silylated, U.S. Pat. No. 6,051,745 the use of nitried SAPO-34 catalysts. In EP 418142 a nickel-modified SAPO-34 is claimed to achieve a very high selectivity to ethylene.

Many efforts have also been made to improve selectivity towards ethylene by various physic-chemical modifications of these small pore materials. The SAPO-34 molecular sieve after incorporating transition metals such as nickel in the framework has been found to yield high ethylene selectivity in the methanol-to-olefins (MTO) process. The higher selectivity is attributed to framework distortion and acidity modification after the incorporation of nickel. Since MTO conversion on microporous silico-aluminophosphates is particularly well-suited for the application of molecular-level concepts to the development of well-defined supported catalysts and the active site of a typical MTO catalyst is a nm-size inorganic cage with an essential organic component, opportunities for altering the selectivity of such catalysts include tailoring the organic component and modification of the cage with additional inorganic material through ship-in-a-bottle synthesis. U.S. Pat. No. 7,078,364 for example concerns the development of a phosphate-modified catalyst.

Zhang, J. in Microporous and Mesoporous Materials 2008, 111, pp. 478-487 concerns alkaline-earth metal cation exchanged chabazite zeolites and to their use for adsorption based $CO_2$ capture. Ji, Y. et al. in ACS Catalysis 2015, 5, pp. 4456-4465 relates to a zeolite of the CHA structure type prepared by the hydrothermal conversion of faujasite and to its use as a catalyst in an MTO reaction. Yarulina, I. et al. in Catal. Sci. Technol. 2016, 6, 2663-2678 concerns the use of zeolite catalysts of the DDR structure type in MTO. Itakura, M et al. in Microporous and Mesoporous Materials 2011, 144, 91-96 relates to the synthesis of high-silica CHA type zeolites from interzeolite conversion of FAU type zeolite and to its use in the conversion of ethanol to light olefins.

Despite the aforementioned advances, there remains the need for providing improved and/or alternative catalysts displaying the high activity and high selectivity in the conversion of methanol to olefins.

DETAILED DESCRIPTION

It was therefore the object of the present invention to provide an alternative and improved catalyst for the conversion of oxygenates containing feeds, and in particular of methanol and/or dimethylether to olefins, particularly with respect to C2-C4 olefins. Thus, it has quite surprisingly been found that zeolites of the CHA type which do not contain phosphorous in their framework structure provide high activity and high selectivity in the conversion of oxygenates to olefins and in particular of methanol and/or dimethyl ether to light olefins when said zeolites contained one or more alkaline earth metals. In particular, it has quite unexpectedly been found that by treating zeolitic materials which do not contain phosphorous in their framework structure with one or more alkaline earth metals, the time on stream thereof in the conversion of oxygenates to olefins may be greatly increased to an extent comparable to that observed for known SAPO-materials. Furthermore, it has surprisingly been found that a considerably improved selectivity towards particular olefins may be achieved, in particular with respect to longer chain light olefins.

Therefore, the present invention relates to a catalyst comprising
one or more metal oxides and/or metalloid oxides and
a zeolitic material having the CHA framework structure comprising $YO_2$ and $X_2O_3$, wherein Y is a tetravalent element and X is a trivalent element, wherein the zeolitic material comprises one or more alkaline earth metals selected from the group consisting of Mg, Ca, Sr, Ba, and combinations of two or more thereof, and
wherein the framework of the zeolitic material comprised in the catalyst contains substantially no phosphorous.

According to the present invention, no particular restrictions apply relative to the one or more alkaline earth metals comprised in the zeolitic material, provided that they are selected from the group consisting of Mg, Ca, Sr, and Ba, including any combination of two or more thereof. It is, however, preferred according to the present invention that the one or more alkaline earth metals are selected from the group consisting of Mg, Ca, and Sr, including any combination of two or more thereof. More preferably, the one or more alkaline earth metals comprise Mg and/or Ca, wherein more preferably the one or more alkaline earth metals comprise Mg. According to the present invention it is further preferred that the zeolitic material contains Mg and/or Ca as the one or more alkaline earth metals, wherein more preferably the zeolitic material comprises Mg as the one or more alkaline earth metals.

According to the present invention, the framework of the zeolitic material contained in the catalyst contains substantially no phosphorous. Within the meaning of the present invention, "substantially" as employed in the present invention with respect to the amount of phosphorous contained in the framework of the zeolitic material indicates an amount of 0.1 wt.-% or less of phosphorous calculated as the element and based on 100 wt.-% of $YO_2$ in the zeolitic material, preferably 0.05 wt.-% or less, more preferably 0.001 wt.-% or less, more preferably 0.0005 wt.-% or less, and more preferably 0.0001 wt.-% or less thereof. Within the meaning of the present invention, the definition of phosphorous substantially not being contained in the framework of the zeolitic material comprises both elemental phosphorous as well as phosphorous containing compounds, wherein in either case the amount of phosphorous is calculated as the element, i.e. irrespective of whether it is actually contained in elemental form or if it is contained as a compound in the zeolitic material.

It is further preferred according to the present invention that the zeolitic material contained in the inventive catalyst contains substantially no phosphorous. Within the meaning of the present invention, "substantially" as employed in the present invention with respect to the amount of phosphorous contained in the zeolitic material indicates an amount of 0.1 wt.-% or less of phosphorous calculated as the element and based on 100 wt.-% of $YO_2$ in the zeolitic material, and preferably 0.05 wt.-% or less, more preferably 0.001 wt.-% or less, more preferably 0.0005 wt. % or less, and even more preferably 0.0001 wt.-% or less thereof. Within the meaning of the present invention, the definition of phosphorous substantially not being contained in the zeolitic material comprises both elemental phosphorous as well as phosphorous containing compounds, wherein again in either case the amount of phosphorous is calculated as the element, i.e. irrespective of whether it is actually contained in elemental form or if it is contained as a compound in the zeolitic material.

Furthermore, it is preferred according to the present invention that the inventive catalyst itself contains substantially no phosphorous. Within the meaning of the present invention, "substantially" as employed in the present invention with respect to the amount of phosphorous contained in the catalyst indicates an amount of 0.1 wt.-% or less of phosphorous calculated as the element and based on 100 wt.-% of the catalyst, preferably 0.05 wt.-% or less, more preferably 0.001 wt.-% or less, more preferably 0.0005 wt.-% or less, and even more preferably 0.0001 wt.-% or less thereof. Within the meaning of the present invention, the definition of phosphorous substantially not being contained in the catalyst comprises both elemental phosphorous as well as phosphorous containing compounds, wherein again in either case the amount of phosphorous is calculated as the element, i.e. irrespective of whether it is actually contained in elemental form or if it is contained as a compound in the zeolitic material.

According to the present invention, the catalyst comprises one or more metal oxides and/or one or more metalloid oxides. Within the meaning of the present invention, the metal oxides and/or metalloid oxides are binary metal oxides and/or binary metalloid oxides, including mixtures and mixed oxides of binary metal oxides and/or binary metalloid oxides. In particular, within the meaning of the present invention, the metal oxides and/or metalloid oxides are not zeolitic materials. Preferably, within the meaning of the present invention, the metal oxides and/or metalloid oxides are amorphous binary metal oxides and/or amorphous binary metalloid oxides, including amorphous mixtures and amorphous mixed oxides of binary metal oxides and/or binary metalloid oxides. Within the meaning of the present invention, the term "amorphous" with respect to a compound or material indicates that said compound or material is non-crystalline such that the X-ray diffractogramm of said compound or material does not display discrete reflections.

In principle, no restrictions apply according to the present invention as to how the one or more metal oxides and/or metalloid oxides and the zeolitic material having the CHA framework structure are provided in the inventive catalyst. It is, however, preferred according to the present invention that the one or more metal oxides and/or metalloid oxides and the zeolitic material having the CHA framework structure are provided such that at least a portion thereof is respectively in physical contact with one another, wherein more preferably the one or more metal oxides and/or metalloid oxides and the zeolitic material having the CHA framework structure are in physical contact with one another in the inventive catalyst. For achieving physical contact within the meaning of the present invention, the components are provided such that they are in physical contact with one another such as is the case in a physical mixture of the components, or when one of the components is supported on the other component and/or vice versa. In the latter case, this would involve supporting the one or more metal oxides and/or metalloid oxides on the zeolitic material as the support or vice versa the supporting of the zeolitic material on the one or more metal oxides and/or metalloid oxides as the support. According to the present invention it is however preferred that the one or more metal oxides and/or metalloid oxides and the zeolitic material are comprised as a composite in the inventive catalyst, wherein more preferably the one or more metal oxides and/or metalloid oxides and the zeolitic material are homogenously distributed within the composite, in which they are accordingly in physical contact with one another. According to the present invention it is further preferred that the inventive catalyst consists of a composite of the one or more metal oxides and/or metalloid oxides and the zeolitic material, wherein preferably the one or more metal oxides and/or metalloid oxides and the zeolitic material are homogenously distributed within the composite.

Accordingly, it is preferred according to the present invention that the catalyst comprises a composite of the zeolitic material and the one or more metal oxides and/or metalloid oxides, wherein preferably the catalyst comprises a homogeneous composite of the zeolitic material and the one or more metal oxides and/or metalloid oxide, wherein more preferably the catalyst consists of a composite of the zeolitic material and the one or more metal oxides and/or metalloid oxide.

Concerning the amount in which the one or more alkaline earth metals may be contained in the zeolitic material, no particular restrictions apply. Thus, by way of example the zeolitic material may contain the one or more alkaline earth metals in an amount ranging anywhere from 0.5 to 10 wt.-% calculated as the element and based on 100 wt.-% of the $YO_2$ in the zeolitic material, wherein preferably from 1 to 8 wt.-% of the one or more alkaline earth metals are contained in the zeolitic material, more preferably from 2 to 7 wt.-%, more preferably from 3 to 6 wt.-%, more preferably from 3.5 to 5.5 wt.-%, more preferably from 4 to 5 wt.-%, and more preferably from 4.3 to 4.9 wt.-%. According to the present invention it is particularly preferred that the zeolitic material comprised in the catalyst contains from 4.5 to 4.7 wt.-% of the one or more alkaline earth metals calculated as the element and based on 100 wt.-% of the $YO_2$ in the zeolitic material.

With respect to the form that the catalyst may have, no particular restrictions apply according to the present invention, such that the catalyst may have any suitable form. It is, however, preferred according to the present invention that the catalyst is in the form of a shaped body, wherein preferably the catalyst is in the form of granulates and/or extrudates. According to the present invention it is particularly referred that the catalyst is in the form of extrudates, and more preferably in the form of extrudates of a composite of the composite of the one or more metal oxides and/or metalloid oxides and the zeolitic material, wherein preferably the one or more metal oxides and/or metalloid oxides and the zeolitic material are homogenously distributed within the extrudate.

As for the zeolitic material, in general, there is no restriction as to the amount in which the one or more alkaline earth metals may be contained in the catalyst. Thus, by way of example, the catalyst may contain anywhere from 0.5 to 10 wt.-% calculated as the element and based on 100 wt.-% of the $YO_2$ in the zeolitic material, wherein preferably the catalyst contains from 1 to 8 wt.-% of the one or more alkaline earth metals, more preferably from 2 to 7 wt.-%, more preferably from 3 to 6 wt.-%, more preferably from 3.5 to 5.5 wt.-%, more preferably from 4 to 5 wt.-%, and more preferably from 4.3 to 4.9 wt.-%. According to the present invention it is particularly preferred that the catalyst contains from 4.5 to 4.7 wt.-% of the one or more alkaline earth metals calculated as the element and based on 100 wt.-% of the $YO_2$ in the zeolitic material.

With respect to the form in which the one or more alkaline earth metals are contained in the zeolitic material, no particular restrictions apply. Accordingly, in principle, the one or more alkaline earth metals may be contained in the zeolitic material in elemental form, in the form of a compound such as in the form of a salt, or in ionic form as counter-ion to the framework of the zeolitic material. It is, however, preferred according to the present invention that at least in part the one or more alkaline earth metals are contained in the zeolitic material as counter-ions to the framework of the zeolite, i.e. in the form of extra-framework ions. Within the meaning of the present invention, the term "extra-framework ions" designates ions which are located at the ion exchange sites of the zeolitic material and thus serve to compensate the charge of the zeolitic framework, wherein according to a preferred meaning of the present invention the term "extra-framework ions" designates cations which are located at the ion exchange sites of the zeolitic material and thus serve to compensate the negative charge of the zeolitic framework No particular restrictions apply according to the present invention as to the tetravalent element Y which is comprised as $YO_2$ in the framework of the zeolitic material having the CHA framework structure, provided that it is a tetravalent element and may be contained in the zeolitic framework as $YO_2$. It is, however, preferred according to the present invention that the tetravalent element Y is selected from the group consisting of Si, Sn, Ti, Zr, and Ge, including mixtures of two or more thereof. According to the present invention it is particularly preferred that the tetravalent element Y comprises Si, wherein more preferably the tetravalent element Y is Si.

Same applies accordingly with respect to the trivalent element X which is comprised as $X_2O_3$ in the framework of the zeolitic material having the CHA framework structure. It is however, preferred according to the present invention that the trivalent element X is selected from the group consisting of Al, B, In, and Ga, including mixtures of two or more thereof. According to the present invention it is further preferred that the trivalent element X comprises Al and/or B, wherein more preferably the trivalent element X comprises Al. According to the present invention it is particularly preferred that the trivalent element X is Al and/or B, wherein more preferably the trivalent element X is Al.

Concerning the $YO_2:X_2O_3$ molar ratio displayed by the zeolitic material having the CHA framework structure contained in the catalyst, no particular restrictions apply such that, by way of example, the $YO_2:X_2O_3$ molar ratio may lie in the range of anywhere from 5 to 100. Preferably, the $YO_2:X_2O_3$ molar ratio of the zeolitic material contained in the catalyst is in the range of from 10 to 80, more preferably from 15 to 60, more preferably from 20 to 50, more preferably from 25 to 40, and more preferably from 28 to 35. According to the present invention it is particularly preferred that the zeolitic material contained in the catalyst displays a $YO_2:X_2O_3$ molar ratio which lies in the range of from 30 to 32.

Same applies accordingly with respect to the specific surface area of the zeolitic material comprised in the inventive catalyst which is not particularly restricted and may by way of example range anywhere from 200 to 800 $m^2/g$ as determined according to DIN 66131 or ISO 9277:2010, preferably according to ISO 9277:2010. It is preferred according to the present invention that the specific surface area of the zeolitic material comprised in the inventive catalyst is in the range of from 300 to 750 m²/g, more preferably from 400 to 720 m²/g, more preferably from 450 to 700 m²/g, more preferably from 500 to 680 m²/g, and more preferably from 550 to 650 m²/g. According to the present invention it is particularly preferred that the specific surface area of the zeolitic material comprised in the inventive catalyst is in the range of from 580 to 620 m²/g. Within the meaning of the present invention, the specific surface area of the zeolitic material designates the surface area of the H-form of the calcined zeolitic material and in particular to the H-form of the zeolitic material after calcination thereof at 500° C. in air for 5 h.

According to the present invention, no particular restrictions apply as to the specific type of zeolitic material having the CHA framework structure which may be comprised in the inventive catalyst. Thus, by way of example, the inventive catalyst may comprise one or more zeolites selected from the group consisting of (Ni(deta)₂)-UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, and ZK-14, ZYT-6, including combinations of two or more thereof, wherein preferably the one or more zeolites are selected from the group consisting of (Ni(deta)₂)-UT-6, Chabazite, |Li-Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, and ZYT-6, including combinations of two or more thereof. According to the present invention it is however particularly preferred that the one or more zeolites contained in the inventive catalyst as the zeolitic material having the CHA framework structure comprises chabazite, wherein more preferably the zeolitic material having the CHA framework structure comprised in the catalyst is chabazite.

As concerns the one or more metal oxides and/or metalloid oxides, in principle no particular restrictions apply as to the type and/or number thereof which may be comprised in the inventive catalyst. Thus, by way of example, the one or more metal oxides and/or metalloid oxides comprised in the catalyst may be one or more metal oxides and/or metalloid oxides selected from the group of oxides of Mg, Y, La, Ti, Zr, Hf, Nb, Ta, Al, Ga, Si, and Ge, and mixtures and/or mixed oxides thereof, wherein preferably the one or more metal oxides and/or metalloid oxides are selected from the group consisting of oxides of La, Ti, Zr, Al, and Si, and mixtures and/or mixed oxides thereof. According to the present invention it is however preferred that the one or more metal oxides and/or metalloid oxides comprise $Al_2O_3$ and/or $SiO_2$, and preferably that the one or more metal oxides and/or metalloid oxides comprise $SiO_2$. According to the present invention it is particularly preferred that the inventive catalyst comprises $Al_2O_3$ and/or $SiO_2$ as the one or more metal oxides and/or metalloid oxides, wherein more preferably $SiO_2$ is contained in the inventive catalyst as the one or more metal oxides and/or metalloid oxides.

Thus, it is preferred according to the present invention that the one or more metal oxides and/or metalloid oxides are selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof. According to the present invention it is further preferred that the one or more metal oxides and/or metalloid oxides are selected from the group consisting of silica, alumina, silica-alumina mixed oxides, and mixtures of two or more thereof, more preferably from the group consisting of fumed silica, colloidal silica, silica-alumina, colloidal silica-alumina, and mixtures of two or more thereof, and more preferably from the group consisting of fumed silica, colloidal silica, and mixtures thereof. According to the present invention it is particularly preferred that the one or more metal oxides and/or metalloid oxides are fumed silica and/or colloidal silica, wherein preferably colloidal silica is contained as the one or more metal oxides and/or metalloid oxides in the inventive catalyst.

As regards the relative amounts of the one or more metal oxides and/or metalloid oxides (also designated in the present application as "MO") and of the zeolitic material having the CHA framework structure in the inventive catalyst, no particular restrictions apply. Thus, by way of example, the inventive catalyst may display a MO:zeolite weight ratio of the one or more metal oxides and/or metalloid oxides (MO) to the zeolitic material ranging anywhere from 0.05 to 3 as calculated based on the weight of the calcined metal oxides and/or metalloid oxides and of the calcined zeolitic material which are accordingly devoid of any alkaline earth metal, respectively, and in particular based on the weight of the respective materials after calcination thereof at 500° C. in air for 5 h, respectively. It is however preferred according to the present invention that the inventive catalyst displays a MO:zeolite weight ratio of the one or more metal oxides and/or metalloid oxides to the zeolitic material which is in the range of from 0.1 to 2, more preferably from 0.15 to 1.5, more preferably from 0.2 to 1, more preferably from 0.25 to 0.8, more preferably from 0.3 to 0.6, more preferably from 0.35 to 0.55, more preferably from 0.38 to 0.5, and more preferably from 0.4 to 0.46. According to the present invention it is particularly preferred that the MO:zeolite weight ratio of the one or more metal oxides and/or metalloid oxides to the zeolitic material is in the range of from 0.42 to 0.44 calculated based on the weight of the calcined metal oxides and/or metalloid oxides and of the calcined zeolitic material.

In general, within the meaning of the present invention, unless specified otherwise, the term "calcined" indicates the state of a material after having been subject to calcination in air employing a heating rate of 2° C./min up to a temperature of 500° C., at which the material is held for a duration of 5 h.

As for the zeolitic material, no particular restrictions apply with respect to the surface area of the inventive catalyst. Thus, by way of example, the specific surface area of the catalyst as determined according to DIN 66131 or ISO 9277:2010, preferably according to ISO 9277:2010, may range anywhere from 100 to 700 m²/g, wherein preferably the specific surface of the catalyst is in the range of from 250 to 500 m²/g, more preferably from 200 to 475 m²/g, more preferably from 250 to 450 m²/g, more preferably from 300 to 425 m²/g, and more preferably from 325 to 400 m²/g. Accordingly to the present invention it is particularly preferred that the specific surface area of the catalyst is in the range of from 350 to 375 m²/g. Within the meaning of the present invention, the specific surface area of the zeolitic material designates the specific surface area of the calcined catalyst, and in particular of the inventive catalyst after calcination thereof at 500° C. in air for 5 h.

Same applies according with respect to the specific pore volume of the catalyst which as for the specific surface area is not particularly restricted. Thus, by way of example, the specific pore volume of the inventive catalyst as determined according to DIN 66133, ISO 15901-1:2016, or ISO 15901-2:2016, preferably by ISO 15901-1:2016, may be in the range of anywhere from 0.1 to 0.7 ml/g, wherein preferably the specific pore volume of the catalyst is in the range of from 0.2 to 0.5 ml/g, more preferably from 0.3 to 0.45 ml/g, more preferably from 0.33 to 0.4 ml/g, and more preferably from 0.35 to 0.38 ml/g. According to the present invention it is particularly preferred that the specific pore volume of the catalyst is in the range of from 0.36 to 0.37 ml/g. Again, within the meaning of the present invention, the specific pore volume of the zeolitic material designates the specific pore volume of the calcined catalyst, and in particular of the inventive catalyst after calcination thereof at 500° C. in air for 5 h.

The present invention further relates to a process for the preparation of a catalyst and in particular to a process for the preparation of the inventive catalyst according to any of the particular and preferred embodiments as defined in the present application. Thus, the present invention further relates to a process for the preparation of a catalyst comprising one or more alkaline earth metals selected from the group consisting of Mg, Ca, Sr, Ba, and combinations of two or more thereof, preferably of a catalyst according to any of the particular and preferred embodiments as defined in the present application, said process comprising (A) providing a zeolitic material having the CHA framework structure comprising $YO_2$ and $X_2O_3$, wherein Y is a tetravalent element and X is a trivalent element, wherein the framework of the zeolitic material contains substantially no phosphorous, and wherein the zeolitic material optionally comprises one or more alkaline earth metals;

(B) mixing the zeolitic material provided in (A) with one or more metal oxides and/or metalloid oxides and with a solvent system;

(C) optionally homogenizing the mixture obtained in (B);

(D) molding of the mixture obtained in (B) or (C);

(E) optional drying of the molding obtained in (D);

(F) optional calcining of the molding obtained in (D) or (E);

(G) optional impregnation of the molding obtained in (D), (E), or (F) with a solution containing one or more salts of the one or more alkaline earth metals;

(H) optional drying of the molding obtained in (G); and (I) optional calcining of the molding obtained in (G) or (H);

wherein the one or more alkaline earth metals in (A) and/or (G) are selected from the group consisting of Mg, Ca, Sr, Ba, and combinations of two or more thereof, preferably from the group consisting of Mg, Ca, Sr, and combinations of two or more thereof, wherein more preferably the one or more alkaline earth metals is Mg and/or Ca, preferably Mg.

According to the inventive process, the zeolitic material provided in (A) preferably comprises one or more alkaline earth metals, wherein the alkaline earth metals are selected from the group consisting of Mg, Ca, Sr, and Ba, including combinations of two or more thereof. As regards the amount in which the zeolitic material provided in (A) contains the one or more alkaline earth metals, no particular restrictions apply according to the present invention such that by way of example the zeolitic material provided in (A) may contain the one or more alkaline earth metals in an amount in the range of from 0.5 to 10 wt.-% calculated as the element and based on 100 wt.-% of the $YO_2$ in the zeolitic material, wherein preferably the zeolitic material provided in (A) contains the one or more alkaline earth metals in an amount in the range from 1 to 8 wt.-%, more preferably from 2 to 7 wt.-%, more preferably from 3 to 6 wt.-%, more preferably from 3.5 to 5.5 wt.-%, more preferably from 4 to 5 wt.-%, and more preferably from 4.3 to 4.9 wt.-%. According to the present invention it is particularly preferred that the zeolitic material provided in (A) contains the one or more alkaline earth metals in an amount in the range of from 4.5 to 4.7 wt.-% calculated as the element and based on 100 wt.-% of the $YO_2$ in the zeolitic material.

With respect to the form in which the one or more alkaline earth metals are preferably contained in the zeolitic material provided in (A), no particular restrictions apply. Accordingly, in principle, the one or more alkaline earth metals may be contained in the zeolitic material in elemental form, in the form of a compound such as in the form of a salt, or in ionic form as counter-ion to the framework of the zeolitic material. It is, however, preferred according to the present invention that at least in part the one or more alkaline earth metals are contained in the zeolitic material provided in (A) as counter-ions to the framework of the zeolite, i.e. in the form of extra-framework ions.

According to the inventive process, the framework of the zeolitic material provided in (A) contains substantially no phosphorous. According to the inventive process it is preferred that the zeolitic material provided in (A) contains substantially no phosphorous.

No particular restrictions apply according to the present invention as to the tetravalent element Y which is comprised as $YO_2$ in the framework of the zeolitic material having the CHA framework structure provided in (A), provided that it is a tetravalent element and may be contained in the zeolitic framework as $YO_2$. It is, however, preferred according to the present invention that the tetravalent element Y is selected from the group consisting of Si, Sn, Ti, Zr, and Ge, including mixtures of two or more thereof. According to the present invention it is particularly preferred that the tetravalent element Y comprises Si, wherein more preferably the tetravalent element Y is Si.

Same applies accordingly with respect to the trivalent element X which is comprised as $X_2O_3$ in the framework of the zeolitic material having the CHA framework structure provided in (A). It is however, preferred according to the present invention that the trivalent element X is selected from the group consisting of Al, B, In, and Ga, including mixtures of two or more thereof. According to the present invention it is further preferred that the trivalent element X comprises Al and/or B, wherein more preferably the trivalent element X comprises Al. According to the present invention it is particularly preferred that the trivalent element X is Al and/or B, wherein more preferably the trivalent element X is Al.

Concerning the $YO_2:X_2O_3$ molar ratio displayed by the zeolitic material having the CHA framework structure provided in (A), no particular restrictions apply such that, by way of example, the $YO_2:X_2O_3$ molar ratio may lie in the range of anywhere from 5 to 100. Preferably, the $YO_2:X_2O_3$ molar ratio of the zeolitic material provided in (A) is in the range of from 10 to 80, more preferably from 15 to 60, more preferably from 20 to 50, more preferably from 25 to 40, and more preferably from 28 to 35. According to the present invention it is particularly preferred that the zeolitic material provided in (A) displays a $YO_2:X_2O_3$ molar ratio which lies in the range of from 30 to 32.

Same applies accordingly with respect to the specific surface area of the zeolitic material provided in (A) which is not particularly restricted and may by way of example range anywhere from 200 to 800 m²/g as determined according to DIN 66131 or ISO 9277:2010, preferably according to ISO 9277:2010. It is preferred according to the present invention that the specific surface area of the zeolitic material provided in (A) is in the range of from 300 to 750 m$^2$/g, more preferably from 400 to 720 m$^2$/g, more preferably from 450 to 700 m$^2$/g, more preferably from 500 to 680 m$^2$/g, and more preferably from 550 to 650 m$^2$/g. According to the present invention it is particularly preferred that the specific surface area of the zeolitic material provided in (A) is in the range of from 580 to 620 m$^2$/g.

According to the present invention, no particular restrictions apply as to the specific type of zeolitic material having the CHA framework structure which may be provided in (A). Thus, by way of example, the zeolitic material having the CHA framework structure provided in (A) may comprise one or more zeolites selected from the group consisting of (Ni(deta)$_2$)-UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, and ZK-14, ZYT-6, including combinations of two or more thereof, wherein preferably the one or more zeolites are selected from the group consisting of (Ni(deta)$_2$)-UT-6, Chabazite, |Li-Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, and ZYT-6, including combinations of two or more thereof. According to the present invention it is however particularly preferred that the one or more zeolites contained in the zeolitic material having the CHA framework structure provided in (A) comprises chabazite, wherein more preferably the zeolitic material having the CHA framework structure provided in (A) is chabazite.

In step (B) of the inventive process, the zeolitic material provided in (A) is mixed with one or more metal oxides and/or metalloid oxides and with a solvent system. As to the solvent system which may be employed in the inventive process, no particular restriction applies provided that a catalyst may be prepared, and in particular that a catalyst according to any of the particular and preferred embodiments of the present invention may be prepared. Thus, the solvent system may comprise one or more solvents, wherein preferably the solvent system comprises one or more hydrophilic solvents, the hydrophilic solvents preferably being selected from the group consisting of polar solvents, more preferably from the group consisting of polar protic solvents, wherein more preferably the solvent system comprises one or more polar protic solvents selected from the group consisting of water, alcohols, carboxylic acids, and mixtures of two or more thereof. According to the inventive process it is further preferred that the solvent system comprises one or more polar protic solvents selected from the group consisting of water, C1-C5 alcohols, C1-C5 carboxylic acids, and mixtures of two or more thereof, more preferably from the group consisting of water, C1-C4 alcohols, C1-C4 carboxylic acids, and mixtures of two or more thereof, more preferably from the group consisting of water, C1-C3 alcohols, C1-C3 carboxylic acids, and mixtures of two or more thereof, and more preferably from the group consisting of water, methanol, ethanol, propanol, formic acid, acetic acid, and mixtures of two or more thereof. According to the inventive process it is however further preferred that the solvent system comprises one or more polar protic solvents selected from the group consisting of water, ethanol, acetic acid, and mixtures of two or more thereof, wherein more preferably the solvent system comprises water and/or ethanol, and wherein more preferably the solvent system comprises water. According to the inventive process, it is however particularly preferred that the solvent system employed in (B) consists of water and/or ethanol, wherein more preferably the solvent system consists of water, preferably of distilled water.

As concerns the one or more metal oxides and/or metalloid oxides in (B), in principle no particular restrictions apply as to the type and/or number thereof which may be employed in the inventive process. Thus, by way of example, the one or more metal oxides and/or metalloid oxides in (B) may be one or more metal oxides and/or metalloid oxides selected from the group of oxides of Mg, Y, La, Ti, Zr, Hf, Nb, Ta, Al, Ga, Si, and Ge, and mixtures and/or mixed oxides thereof, wherein preferably the one or more metal oxides and/or metalloid oxides are selected from the group consisting of oxides of La, Ti, Zr, Al, and Si, and mixtures and/or mixed oxides thereof. According to the inventive process it is however preferred that the one or more metal oxides and/or metalloid oxides comprise Al$_2$O$_3$ and/or SiO$_2$, and preferably that the one or more metal oxides and/or metalloid oxides comprise SiO$_2$. According to the inventive process it is particularly preferred that one or more metal oxides and/or metalloid oxides in (B) are Al$_2$O$_3$ and/or SiO$_2$, wherein more preferably SiO$_2$ is used as the one or more metal oxides and/or metalloid oxides in (B).

Thus, it is preferred according to the inventive process that the one or more metal oxides and/or metalloid oxides in (B) are selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof. According to the present invention it is further preferred that the one or more metal oxides and/or metalloid oxides in (B) are selected from the group consisting of silica, alumina, silica-alumina mixed oxides, and mixtures of two or more thereof, more preferably from the group consisting of fumed silica, colloidal silica, silica-alumina, colloidal silica-alumina, and mixtures of two or more thereof, and more preferably from the group consisting of fumed silica, colloidal silica, and mixtures thereof. According to the present invention it is particularly preferred that the one or more metal oxides and/or metalloid oxides in (B) are fumed silica and/or colloidal silica, wherein preferably colloidal silica is used as the one or more metal oxides and/or metalloid oxides in (B).

As regards the relative amounts of the one or more metal oxides and/or metalloid oxides (MO) and of the zeolitic material having the CHA framework structure in the mixture obtained in (B), no particular restrictions apply provided that a catalyst, and in particular a catalyst according to any of the particular and preferred embodiments of the invention as defined in the present application may be obtained according to the inventive process. Thus, by way of example, the mixture obtained in (B) may display a MO:zeolite weight ratio of the one or more metal oxides and/or metalloid oxides to the zeolitic material ranging anywhere from 0.05 to 3 as calculated based on the weight of the calcined metal oxides and/or metalloid oxides and of the calcined zeolitic material which is devoid of any alkaline earth metals, respectively, and in particular based on the weight of the respective materials after calcination thereof at 500° C. in air for 5 h, respectively. It is however preferred according to the present invention that the mixture obtained in (B) displays a MO:zeolite weight ratio of the one or more metal oxides and/or metalloid oxides to the zeolitic material which is in the range of from 0.1 to 2, more preferably from 0.15 to 1.5, more preferably from 0.2 to 1, more preferably from 0.25 to 0.8, more preferably from 0.3 to 0.6, more preferably from 0.35 to 0.55, more preferably from 0.38 to 0.5, and more preferably from 0.4 to 0.46. According to the present invention it is particularly preferred that the MO:zeolite weight ratio of the one or more metal oxides and/or metalloid oxides to the zeolitic material in the mixture obtained in (B) is in the range of from 0.42 to 0.44 calculated based on the weight of the calcined metal oxides and/or metalloid oxides and of the calcined zeolitic material.

Same applies accordingly with respect to the amounts of the solvent system in (B) which may adopt any suitable values provided that a catalyst, and in particular a catalyst according to any of the particular and preferred embodiments of the invention as defined in the present application may be obtained according to the inventive process. Thus, by way of example, the mixture obtained in (B) of the inventive process may display a solvent system:zeolitic material weight ratio of the solvent system to the zeolitic material ranging anywhere from 0.5 to 2 as calculated based on the weight of the calcined zeolitic material which is devoid of any alkaline earth metals, wherein preferably the solvent system:zeolitic material weight ratio is in the range of from 0.8 to 1.7, more preferably from 1.0 to 1.5, and more preferably from 1.1 to 1.4. According to the inventive process it is particularly preferred that the mixture obtained in (B) of the inventive process displays a solvent system: zeolitic material weight ratio in the range of from 1.2 to 1.3.

In principle, there is no restriction as any further components which may be further added in (B) in addition to the zeolitic material, the one or more metal oxides and/or metalloid oxides and the solvent system. Thus, although it is alternatively preferred according to the present invention that the mixture obtained in (B) consists of the zeolitic material optionally comprising one or more alkaline earth metals, the one or more metal oxides and/or metalloid oxides and the solvent system, (B) may further comprise mixing said components with one or more further components. Thus, by way of example (B) may further comprise mixing the zeolitic material optionally comprising one or more alkaline earth metals, the one or more metal oxides and/or metalloid oxides and the solvent system with one or more pore forming agents, wherein the one or more pore forming agents are preferably selected from the group consisting of polymers, carbohydrates, graphite, and mixtures of two or more thereof. According to the present invention it is further preferred that the one or more pore forming agents are selected from the group consisting of polymeric vinyl compounds, polyalkylene oxides, polyacrylates, polyolefins, polyamides, polyesters, cellulose and cellulose derivatives, sugars, and mixtures of two or more thereof, more preferably from the group consisting of polystyrene, C2-C3 polyalkylene oxides, cellulose derivatives, sugars, and mixtures of two or more thereof, more preferably from the group consisting of polystyrene, polyethylene oxide, C1-C2 hydroxyalkylated and/or C1-C2 alkylated cellulose derivatives, sugars, and mixtures of two or more thereof, and more preferably from the group consisting of polystyrene, polyethylene oxide, hydroxyethyl methyl cellulose, and mixtures of two or more thereof. According to the inventive process it is particularly preferred that the one or more pore forming agents consists of one or more selected from the group consisting of polystyrene, polyethylene oxide, hydroxyethyl methyl cellulose, and mixtures of two or more thereof, wherein more preferably the one or more pore forming agents consist of hydroxyethyl methyl cellulose.

According to any of the particular and preferred embodiments of the inventive process wherein (B) further comprises mixing with one or more pore forming agents, there is principally no restriction as to the amount of the one or more pore forming agents which may be used provided that a catalyst, and in particular a catalyst according to any of the particular and preferred embodiments of the invention as defined in the present application may be obtained according to the inventive process. Thus, by way of example, the mixture obtained in (B) may display a pore forming agent: zeolitic material weight ratio of the one or more pore forming agents to the zeolitic material in the range of anywhere from 0.001 to 0.3, as calculated based on the weight of the calcined zeolitic material which is devoid of any alkaline earth metals, wherein preferably the pore forming agent:zeolitic material weight ratio in (B) is in the range of from 0.005 to 0.2, more preferably from 0.01 to 0.15, more preferably from 0.02 to 0.12, more preferably from 0.03 to 0.09, more preferably from 0.035 to 0.07, and more preferably from 0.04 to 0.06. According to the inventive process it is particularly preferred that the mixture obtained in (B) displays a pore forming agent:zeolitic material weight ratio in the range of from 0.045 to 0.055.

According to the inventive process, the mixture obtained in (B) is preferably homogenized in (C). As regards the means of homogenization in (C), no particular restrictions apply, provided that a homogenized mixture may be obtained according to the inventive process. Accordingly, any method suitable to this effect may be employed, wherein according to the inventive process it is preferred that homogenizing of the mixture in (C) involves the kneading of the mixture obtained in (B).

It is preferred according to the inventive process that the mixture obtained in (B) or (C) is molded in (D). Again, no restrictions apply as to the method which may be used for molding, wherein it is preferred according to the inventive process that molding of the mixture in (D) involves extruding or spray granulating of the mixture obtained in (B) or (C), preferably extruding.

According to the inventive process, the molding obtained in (D) is preferably dried in (E). Drying may be achieved by any suitable means and under any suitable conditions, wherein it is preferred that drying in (E) is effected at a temperature in the range from 50 to 220° C., and preferably at a temperature in the range of from 70 to 180° C., more preferably from 80 to 150° C., more preferably from 90 to 130° C., and more preferably from 100 to 125° C. According to the present invention, it is particularly preferred that the molding obtained in (D) is dried in (E) at a temperature in the range of from 110 to 120° C.

It is preferred according to the inventive process that the molding obtained in (D) or (E) is calcined in (F). In principle, calcining in (F) may be performed under any suitable conditions and for any suitable duration provided that a catalyst, and in particular a catalyst according to any of the particular and preferred embodiments of the invention as defined in the present application may be obtained according to the inventive process. Thus, by way of examples, calcining of the molding in (F) may be performed at a temperature in the range of anywhere from 300 to 850° C., wherein preferably calcining is performed at a temperature in the range of from 350 to 750° C., more preferably from 400 to 700° C., more preferably from 450 to 650° C., and more preferably from 475 to 600° C. According to the inventive process it is particularly preferred in (F) that the molding obtained in (D) or (E) is calcined at a temperature in the range of from 500 to 550° C.

In the inventive process, it is preferred that the molding obtained in (D), (E), or (F) is impregnated with a solution containing one or more salts of the one or more alkaline earth metals. In principle, any suitable method of impregnation employing any suitable solution of the one or more alkaline earth metals may be employed to this effect. Thus, as regards the solution employed in (G), no particular restrictions apply relative to the type or number not with respect to the amount of solvent or solvents which may be employed, proved that the one or more alkaline earth metal salts may be at least partly dissolved in the solvent or solvents, wherein preferably the one or more alkaline earth metal salts are entirely dissolved in the solvent or solvents used. To this effect, it is preferred that the solution used in (G) comprises one or more solvents selected from the group consisting of alcohols, water, mixtures of two or more alcohols, and mixtures of water and one or more alcohols, wherein preferably the one or more solvents are selected from the group consisting of ($C_1$-$C_6$) alcohols, water, mixtures of two or more ($C_1$-$C_6$) alcohols, and mixtures of water and one or more ($C_1$-$C_6$) alcohols. According to the inventive process it is further preferred that the one or more solvents are selected from the group consisting of ($C_1$-$C_4$) alcohols, water, mixtures of two or more ($C_1$-$C_4$) alcohols, and mixtures of water and one or more ($C_1$-$C_4$) alcohols, more preferably from the group consisting of methanol, ethanol, n-propanol, isopropanol, water and mixtures of two or more thereof. It is particularly preferred according to the inventive process that the solution used in (G) comprises one or more solvents selected from the group consisting of methanol, ethanol, water and mixtures of two or more thereof, the solvent more preferably being water, preferably distilled water.

According to the inventive process, the molding obtained in (G) is preferably dried in (H). Again, as for (E), drying may be achieved by any suitable means and under any suitable conditions, wherein it is preferred that drying in (H) is effected at a temperature in the range from 50 to 220° C., and preferably at a temperature in the range of from 70 to 180° C., more preferably from 80 to 150° C., more preferably from 90 to 130° C., and more preferably from 100 to 125° C. According to the present invention, it is particularly preferred that the molding obtained in (G) is dried in (H) at a temperature in the range of from 110 to 120° C.

It is preferred according to the inventive process that the molding obtained in (G) or (H) is calcined in (I). In principle, calcining in (I) may be performed under any suitable conditions and for any suitable duration provided that a catalyst, and in particular a catalyst according to any of the particular and preferred embodiments of the invention as defined in the present application may be obtained according to the inventive process. Thus, by way of examples, calcining of the molding in (I) may be performed at a temperature in the range of anywhere from 300 to 850° C., wherein preferably calcining is performed at a temperature in the range of from 350 to 750° C., more preferably from 400 to 700° C., more preferably from 450 to 650° C., and more preferably from 475 to 600° C. According to the inventive process it is particularly preferred in (I) that the molding obtained in (G) or (H) is calcined at a temperature in the range of from 500 to 550° C.

The inventive process for the preparation of a catalyst is not particularly restricted with respect to steps which it may further contain, and in particular relative to the steps which it may comprise prior to, in between, and subsequent to step (A) to (I). Thus, by way of example, it is preferred that the inventive process further comprises (J) subjecting the molding obtained in (F) and/or (I), and preferably subjecting the molding obtained in (I), to a hydrothermal treatment.

As regards the preferred hydrothermal treatment, no particular restrictions apply with respect to the conditions under which said treatment is performed. It is, however, preferred that in (J) the hydrothermal treatment of the molding obtained in (F) and/or (I), and in particular of the molding obtained in (I) in (J) is conducted under autogenous pressure. As regards the temperature under which the preferred hydrothermal treatment is conducted, no particular restrictions apply such that said treatment may be performed at any suitable temperature. Thus, by way of example, the preferred hydrothermal treatment may be conducted at a temperature in the range of anywhere from 80 to 200° C., wherein preferably the temperature of the hydrothermal treatment is in the range of from 90 to 180° C., more preferably from 100 to 170° C., and more preferably from 110 to 160° C. According to the inventive process, it is particularly preferred that the hydrothermal treatment is conducted at a temperature in the range of from 120 to 150° C.

No particular restrictions apply with respect to the medium in which the preferred hydrothermal treatment is performed in (J) provided that it comprises water. Thus, by way of example, the preferred hydrothermal treatment may be performed with a water containing solvent system and/or with an aqueous solution. It is, however, particularly preferred according to the inventive process that the hydrothermal treatment is performed with distilled water.

As concerns the duration of the preferred hydrothermal treatment in (J), again no particular restrictions apply. Thus, by way of example, the hydrothermal treatment in (J) may be performed for a duration ranging anywhere from 1 to 48 hours, wherein preferably the hydrothermal treatment is performed for a duration in the range of from 2 to 36 hours, more preferably from 4 to 24 hours, and more preferably from 5 to 12 hours. According to the inventive process it is particularly preferred that the hydrothermal treatment is performed for a duration in the range of from 2 to 9 hours.

In addition to relating to a catalyst as such, the present invention further relates to a catalyst as obtained according to any of the particular and preferred embodiments of the inventive process. Furthermore, the invention is not only limited to a catalyst directly obtained by the inventive process but further extends to a catalyst as obtainable according to any of the particular and preferred embodiments of the inventive process, i.e. to a catalyst as may be obtained according to any of the particular and preferred embodiments of the inventive process, yet independently of the actual process according to which it was actually obtained, i.e. independently as to whether it was obtained according to the inventive process or according to another process, provided that it displays all of the features of a catalyst which may be obtained according to the inventive process.

Therefore, the present invention further relates to a catalyst obtainable and/or obtained according to any of the particular and preferred embodiments of the inventive process as defined in the present application.

In addition to relating to a catalyst as well as to a process for preparing such a catalyst, the present invention further relates to a method for converting oxygenates to olefins. More particularly, the present invention further relates to a method comprising:

(i) providing a catalyst according to any of the particular and preferred embodiments of the present invention as defined in the present application;

(ii) providing a gas stream comprising one or more oxygenates;

(iii) contacting the catalyst provided in (i) with the gas stream provided in (ii) and converting one or more oxygenates to one or more olefins.

With regard to the oxygenates which can be used in the inventive method, there is in principle no restriction whatsoever, provided that the one or more oxygenates present in the gas stream according to (ii) can be converted by one of the catalysts according to the present invention and especially according to the particular and preferred embodiments thereof to at least one olefin when contacted according to (iii). According to the present invention, however, it is preferable that the one or more oxygenates present in the gas stream according to (ii) are selected from the group consisting of aliphatic alcohols, ethers, carbonyl compounds and mixtures of two or more thereof. Further preferably, the one or more oxygenates are selected from the group consisting of ($C_1$-$C_6$)-alcohols, di($C_1$-$C_3$)alkyl ethers, ($C_1$-$C_6$)-aldehydes, ($C_2$-$C_6$)-ketones and mixtures of two or more thereof, further preferably consisting of ($C_1$-$C_4$)-alcohols, di($C_1$-$C_2$)alkyl ethers, ($C_1$-$C_4$)-aldehydes, ($C_2$-$C_4$)-ketones and mixtures of two or more thereof. In yet further preferred embodiments of the present invention, the gas stream according to (ii) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, the one or more oxygenates further preferably being selected from the group consisting of methanol, ethanol, dimethyl ether, diethyl ether, ethyl methyl ether and mixtures of two or more thereof. In particularly preferred embodiments of the method according to the invention for converting oxygenates to olefins, the gas stream according to (ii) comprises methanol and/or dimethyl ether as the one or more oxygenates, and dimethyl ether is more preferably the oxygenate present in the gas stream according to (ii).

On the other hand, with regard to the content of oxygenates in the gas stream according to (ii) to the method according to the invention for converting oxygenates to olefins, there is no restriction whatsoever according to the present invention here either, provided that, when the gas stream is contacted in (iii) with a catalyst according to the present invention, at least one oxygenate can be converted to at least one olefin. In preferred embodiments, the content of oxygenates in the gas stream according to (ii) is in the range from 2 to 100% by volume based on the total volume, the content especially being based on a gas stream at a temperature in the range from 200 to 700° C. and at a pressure of 101.3 kPa, preferably at a temperature in the range from 250 to 650° C., more preferably from 300 to 600° C., more preferably from 350 to 550° C., more preferably from 400 to 500° C., and more preferably from 425 to 475° C. and at a pressure of 101.3 kPa. According to the present invention, it is further preferred that the content of oxygenates in the gas stream according to (ii) is in the range from 10 to 99% by volume, further preferably from 3 to 99% by volume, more preferably from 4 to 95% by volume, more preferably from 5 to 80% by volume, more preferably from 6 to 50% by volume, more preferably from 7 to 40% by volume, preferably from 8 to 30% by volume, and more preferably from 9 to 20% by volume. In particularly preferred embodiments of the method according to the invention for converting oxygenates to olefins, the content of oxygenates in the gas stream according to (ii) is in the range from 10 to 15% by volume.

With regard to the further components which may be present in the gas stream according to (ii) in the method according to the invention, there is in principle no restriction whatsoever, provided that the gas stream is suitable overall for converting at least one of the oxygenates to at least one olefin in step (iii) when contacted with a catalyst according to the present invention. According to the present invention, it is particularly preferred that the gas stream according to (ii) of the method according to the invention comprises water.

With regard to those preferred embodiments in which, as well as the one or more oxygenates, water is present in the gas stream according to (ii), there is no restriction in principle with respect to the water content which may be present therein, provided that the conversion of at least one oxygenate in the gas stream to at least one olefin in step (iii) of the contacting of the gas stream can be effected with a catalyst according to the present invention. In these preferred embodiments, however, it is preferable that the water content in the gas stream is in the range from 5 to 60% by volume based on the total volume, the water content more preferably being in the range from 10 to 55% by volume, further preferably from 20 to 45% by volume and further preferably from 30 to 40% by volume.

Thus, according to the present invention, preference is given to embodiments of the method for converting oxygenates to olefins in which water is present in the gas stream according to (ii), preferably in the range from 5 to 60% by volume based on the total volume, preferably from 10 to 55% by volume, further preferably from 20 to 50% by volume, and further preferably from 30 to 45% by volume.

According to the inventive method for converting oxygenates to olefins, it is preferred that the gas stream provided in (ii) originates from a preliminary reaction, preferably from the conversion of one or more alcohols to one or more ethers, especially from the conversion of one or more alcohols selected from the group consisting of methanol, ethanol, n-propanol, isopropanol and mixtures of two or more thereof, further preferably from the group consisting of methanol, ethanol, n-propanol and mixtures of two or more thereof, the gas stream provided in (ii) more preferably originating from a preliminary reaction of methanol and/or ethanol and methanol further preferably being at least partly converted to one or more di($C_1$-$C_2$)alkyl ethers, preferably to one or more di($C_1$-$C_2$)alkyl ethers selected from the group consisting of dimethyl ether, diethyl ether, ethyl methyl ether and mixtures of two or more thereof. According to the inventive method it is particularly preferred that the gas stream provided in (ii) originates from a preliminary reaction of conversion of methanol to dimethyl ether.

According to any of the particular and preferred embodiments of the method according to the invention in which the gas stream provided in (ii) originates from a preliminary reaction of one or more alcohols, there is no particular restriction whatsoever in principle with respect to the reaction and hence the reaction product of the conversion of one or more alcohols, provided that this leads to a gas stream comprising one or more oxygenates which, when contacted in (iii) with a catalyst according to the present invention, enables the conversion of at least one of the oxygenates to at least one olefin. In these particular embodiments, it is further preferable that the preliminary reaction leads to conversion of at least one alcohol to at least one ether and especially to at least one dialkyl ether, the preliminary reaction more preferably being a dehydration in which water is obtained as a coproduct to one or more dialkyl ethers. In the particular and preferred embodiments of the present invention in which the gas stream provided in (ii) originates from a preliminary reaction, it is particularly preferred in the method according to the invention that such a gas stream originating from a preliminary reaction is supplied directly and without workup to the method according to the invention in step (ii).

According to further preferred embodiments of the inventive method, the gas stream provided in (ii) further comprises one or more inert gases. No restrictions apply according to the inventive method as to the type or number, nor with respect to the amount of the one or more inert gases which may be present in the gas stream provided in (ii). Thus, by way of examples, the gas stream provided in (ii) may contain one or more inert gases in an amount ranging anywhere from 0.1 to 90% by volume, wherein more preferably the gas stream contains from 1 to 85% by volume, more preferably from 5 to 80% by volume, more preferably from 10 to 75% by volume, more preferably from 20 to 70% by volume, and more preferably from 40 to 65% by volume. According to the inventive method it is particularly preferred that the gas stream provided in (ii) comprises one or more inert gases in an amount in the range of from 50 to 60% by volume.

With regards to the type of inert gas which may be contained in the gas stream in (ii), again no particular restrictions apply such that the one or more inert gases may by way of example be selected from the group consisting of helium, neon, argon, krypton, nitrogen, carbon monoxide, carbon dioxide, and mixtures of two or more thereof. According to the inventive method it is however preferred that the one or more inert gases comprised in the gas stream in (ii) is selected from the group consisting of argon, nitrogen, carbon dioxide, and mixtures of two or more thereof. According to the inventive method it is further preferred that the one or more inert gases comprise nitrogen, wherein it is particularly preferred that the one or more inert gases is nitrogen.

With respect to the manner of contacting the gas stream with a catalyst according to the present invention in step (iii) of the method according to the invention for converting oxygenates to olefins, there is in principle no restriction whatsoever, provided that the conversion of at least one oxygenate to at least one olefin can be implemented. This applies, for example, to the temperature at which the contacting (iii) takes place. Thus, for example, the contacting in step (iii) of the method according to the invention can take place at a temperature in the range from 200 to 700° C., preference being given to selecting temperatures in the range from 250 to 650° C., further preferably from 300 to 600° C., further preferably from 350 to 550° C., and further preferably from 400 to 500° C. In particularly preferred embodiments of the present invention, the contacting according to (iii) of the method according to the invention is performed at a temperature in the range from 425 to 475° C.

The same applies correspondingly to the pressure at which the gas stream is contacted in step (iii) of the method according to the invention with the catalyst according to the present invention. Thus, the contacting can in principle take place at any desired pressure, provided that this allows the conversion of at least one oxygenate to at least one olefin by virtue of the contacting of the gas stream with the catalyst. Thus, the pressure, for example in the contacting in step (iii), may be in the range from 0.1 to 10 bar, the pressure according to the present application indicating the absolute pressure, such that a pressure of 1 bar in the contacting accordingly corresponds to the standard pressure of 1.03 kPa. According to the present invention, the contacting in step (iii) takes place preferably at a pressure in the range of from 0.3 to 7 bar, further preferably from 0.5 to 5 bar, further preferably from 1 to 4.5 bar, more preferably from 1.3 to 4 bar, more preferably from 1.5 to 3.5 bar, more preferably from 1.8 to 3.3 bar, more preferably from 2.0 to 3.0 bar, and more preferably from 2.2 to 2.8 bar. In particularly preferred embodiments of the method according to the invention for converting oxygenates to olefins, the contacting in step (iii) takes place at a pressure in the range of from 2.4 to 2.6 bar.

In addition, there are no particular restrictions with respect to the manner of performance of the method according to the invention for converting oxygenates to olefins, and so it is possible to use either a continuous or a noncontinuous method, the noncontinuous method being performable, for example, in the form of a batch method. According to the present invention, however, it is preferable to conduct the method according to the invention for the conversion of oxygenates as a continuous method. Thus, according to the present invention, preference is given to embodiments of the method for converting oxygenates to olefins in which the method is a continuous method.

With respect to these preferred embodiments of a continuous method, there are no restrictions whatsoever with respect to the space velocity selected, provided that the conversion of an oxygenate to an olefin can be effected. Thus, it is possible to select, for example, space velocities (GHSV=gas hourly space velocity is calculated as the ratio of oxygenate reactant stream in liters/h to the volume of the reactor in liters) in the contacting in step (iii) which are in the range from 500 to 5,000 $h^{-1}$, preferably from 1,000 to 4,000 $h^{-1}$, more preferably from 1,500 to 3,500 $h^{-1}$, more preferably from 2,000 to 3,000 $h^{-1}$, and more preferably from 2,200 to 2,800 $h^{-1}$. In particularly preferred embodiments of the method according to the invention for converting oxygenates, space velocities for the contacting of the gas stream in step (iii) in the range from 2,400 to 2,600 $h^{-1}$ are selected.

With respect to the preferred space velocities according to the particular embodiments of the method according to the invention for converting oxygenates to olefins, these are preferably established in connection with a conversion of oxygenates within a particular range. Thus, the space velocities according to the particular and preferred embodiments of the method according to the invention may be established at a conversion of oxygenate in the range from, for example, 50 to 99.9%. According to the present invention, the space velocity according to the particular and preferred embodiments, however, is preferably established at a conversion of oxygenates in the range from 70 to 99.5%, further preferably from 90 to 99%, further preferably from 95 to 98.5%, further preferably from 96 to 98% and further preferably 96.5 to 97.5%. According to the present invention, however, it is further preferred that the space velocity in the course of contacting of the gas stream in step (iii) of the method according to the invention is established at a full conversion from 96.5 to 99.9% or more of the oxygenate, further preferably from 97.5 to 99.9% or more, further preferably from 98 to 99.9% or more, further preferably from 99 to 99.9% or more and further preferably from 99.5 to 99.9% or more conversion of oxygenates.

The present invention further relates to the use of the inventive catalyst as described above, and especially to the use of the inventive catalyst according to any of the particular and preferred embodiments as described in the present application. According to the present invention, there is no restriction whatsoever in principle with respect to the use of the inventive catalyst, and so it can be used either for the conversion of oxygenates to olefins or in any conceivable catalytic process in which the catalyst exhibits a corresponding catalytic action with respect to a chemical conversion. According to the present invention, however, the inventive catalyst is preferably used in a methanol-to-olefin process (MTO process), in a dimethylether to olefin process (DTO process), methanol-to-gasoline process (MTG process), in a methanol-to-hydrocarbon process, in a biomass to olefins and/or biomass to aromatics process, in a methane to benzene process, for alkylation of aromatics or in fluid catalytic cracking processes (FCC processes), and preferably in a methanol-to-olefin process (MTO process) and/or in a dimethylether to olefin process (DTO process). According to the present invention it is particularly preferred that the inventive catalyst according to any one of the particular and preferred embodiments as described in the present application is used in a methanol-to-propylene process (MTP process), in a methanol-to-propylene/butylene process (MT3/4 process), in a dimethylether-to-propylene process (DTP process), in a dimethylether-to-propylene/butylene process (DT3/4 process), and/or in a dimethylether-to-ethylene/propylene (DT2/3 process).

The present invention is further illustrated by the following embodiments and combinations of embodiments as indicated by the respective dependencies and back-references. In particular, it is noted that in each instance where reference is made to more than two embodiments, for example in the context of a term such as "The process of any one of embodiments 1 to 4", every embodiment in this range is meant to be explicitly disclosed, i.e. the wording of this term is to be understood as being synonymous to "The process of any one of embodiments 1, 2, 3, and 4".

1. Catalyst comprising
   one or more metal oxides and/or metalloid oxides and
   a zeolitic material having the CHA framework structure comprising $YO_2$ and $X_2O_3$, wherein Y is a tetravalent element and X is a trivalent element, wherein the zeolitic material comprises one or more alkaline earth metals selected from the group consisting of Mg, Ca, Sr, Ba, and combinations of two or more thereof, preferably from the group consisting of Mg, Ca, Sr, and combinations of two or more thereof, wherein more preferably the zeolitic material comprises Mg and/or Ca, preferably Mg, wherein more preferably Mg and/or Ca, preferably Mg is comprised in the zeolitic material as the one or more alkaline earth metals, and
   wherein the framework of the zeolitic material comprised in the catalyst contains substantially no phosphorous.
2. The catalyst of embodiment 1, wherein the catalyst comprises a composite of the zeolitic material and the one or more metal oxides and/or metalloid oxides, wherein preferably the catalyst comprises a homogeneous composite of the zeolitic material and the one or more metal oxides and/or metalloid oxide, wherein more preferably the catalyst consists of a composite of the zeolitic material and the one or more metal oxides and/or metalloid oxide.
3. The catalyst of embodiment 1 or 2, wherein the catalyst contains the one or more alkaline earth metals in an amount in the range of from 0.5 to 10 wt.-% calculated as the element and based on 100 wt.-% of the $YO_2$ in the zeolitic material, preferably from 1 to 8 wt.-%, more preferably from 2 to 7 wt.-%, more preferably from 3 to 6 wt.-%, more preferably from 3.5 to 5.5 wt.-%, more preferably from 4 to 5 wt.-%, more preferably from 4.3 to 4.9 wt.-%, and more preferably from 4.5 to 4.7 wt.-%
4. The catalyst of any of embodiments 1 to 3, wherein the zeolitic material contains substantially no phosphorous, wherein preferably the catalyst contains substantially no phosphorous.
5. The catalyst of any of embodiments 1 to 4, wherein the catalyst is in the form of a shaped body, preferably in the form of granulates and/or extrudates.
6. The catalyst of any of embodiments 1 to 5, wherein the zeolitic material comprised in the catalyst contains the one or more alkaline earth metals in an amount in the range of from 0.5 to 10 wt.-% calculated as the element and based on 100 wt.-% of the $YO_2$ in the zeolitic material, preferably from 1 to 8 wt.-%, more preferably from 2 to 7 wt.-%, more preferably from 3 to 6 wt.-%, more preferably from 3.5 to 5.5 wt.-%, more preferably from 4 to 5 wt.-%, more preferably from 4.3 to 4.9 wt.-%, and more preferably from 4.5 to 4.7 wt.-%.
7. The catalyst of any of embodiments 1 to 6, wherein the one or more alkaline earth metals are contained in the zeolitic material comprised in the catalyst as extra-framework ions.
8. The catalyst of any of embodiments 1 to 7, wherein Y is selected from the group consisting of Si, Sn, Ti, Zr, Ge, and mixtures of two or more thereof, Y preferably being Si.
9. The catalyst of any of embodiments 1 to 8, wherein X is selected from the group consisting of Al, B, In, Ga, and mixtures of two or more thereof, X preferably being Al and/or B, and more preferably being Al.
10. The catalyst of any of embodiments 1 to 9, wherein the zeolitic material comprised in the catalyst displays a $YO_2:X_2O_3$ molar ratio in the range of from 5 to 100, preferably from 10 to 80, more preferably from 15 to 60, more preferably from 20 to 50, more preferably from 25 to 40, more preferably from 28 to 35, and more preferably from 30 to 32.
11. The catalyst of any of embodiments 1 to 10, wherein the zeolitic material comprised in the catalyst displays a specific surface area as determined according to DIN 66131 or ISO 9277:2010, preferably according to ISO 9277:2010, in the range of from 200 to 800 m$^2$/g as determined according to DIN 66131, preferably from 300 to 750 m$^2$/g, more preferably from 400 to 720 m$^2$/g, more preferably from 450 to 700 m$^2$/g, more preferably from 500 to 680 m$^2$/g, more preferably from 550 to 650 m$^2$/g, more preferably from 580 to 620 m$^2$/g.
12. The catalyst of any of embodiments 1 to 11, wherein the zeolitic material comprised in the catalyst comprises one or more zeolites selected from the group consisting of (Ni(deta)$_2$)UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, ZK-14, ZYT-6, and combinations of two or more thereof, preferably from the group consisting of (Ni (deta)$_2$)-UT-6, Chabazite, |Li-Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, ZYT-6, and combinations of two or more thereof, and wherein even more preferably the zeolitic material comprises Chabazite.
13. The catalyst of any of embodiments 1 to 12, wherein the one or more metal oxides and/or metalloid oxides comprised in the catalyst are one or more metal oxides and/or metalloid oxides selected from the group of oxides of Mg, Y, La, Ti, Zr, Hf, Nb, Ta, Al, Ga, Si, and Ge, and mixtures and/or mixed oxides thereof, preferably from the group consisting of oxides of La, Ti, Zr, Al, and Si, and mixtures and/or mixed oxides thereof, wherein more preferably the one or more metal oxides and/or metalloid oxides comprise $Al_2O_3$ and/or $SiO_2$, preferably $SiO_2$, wherein more preferably the catalyst comprises $Al_2O_3$ and/or $SiO_2$, preferably $SiO_2$ as the one or more metal oxides and/or metalloid oxides.

14. The catalyst of embodiment 13, wherein the one or more metal oxides and/or metalloid oxides are selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, and mixtures of two or more thereof, more preferably from the group consisting of fumed silica, colloidal silica, silica-alumina, colloidal silica-alumina, and mixtures of two or more thereof, more preferably from the group consisting of fumed silica, colloidal silica, and mixtures thereof, wherein more preferably the one or more metal oxides and/or metalloid oxides are fumed silica and/or colloidal silica, preferably colloidal silica.

15. The catalyst of any of embodiments 1 to 14, wherein the catalyst displays a MO:zeolite weight ratio of the one or more metal oxides and/or metalloid oxides (MO) to the zeolitic material in the range of from 0.05 to 3 as calculated based on the weight of the calcined metal oxides and/or metalloid oxides and of the calcined zeolitic material, preferably in the range of from 0.1 to 2, more preferably from 0.15 to 1.5, more preferably from 0.2 to 1, more preferably from 0.25 to 0.8, more preferably from 0.3 to 0.6, more preferably from 0.35 to 0.55, more preferably from 0.38 to 0.5, more preferably from 0.4 to 0.46, and more preferably from 0.42 to 0.44.

16. The catalyst of any of embodiments 1 to 15, wherein the specific surface area of the catalyst as determined according to DIN 66131 or ISO 9277:2010, preferably according to ISO 9277:2010, is in the range of from 100 to 700 m²/g, preferably in the range of from 250 to 500 m²/g, more preferably from 200 to 475 m²/g, more preferably from 250 to 450 m²/g, more preferably from 300 to 425 m²/g, more preferably from 325 to 400 m²/g, and more preferably from 350 to 375 m²/g.

17. The catalyst of any of embodiments 1 to 16, wherein the specific pore volume of the catalyst as determined according to DIN 66133, ISO 15901-1:2016, or ISO 15901-2: 2016, preferably by ISO 15901-1:2016, is in the range of from 0.1 to 0.7 ml/g, preferably from 0.2 to 0.5 ml/g, more preferably from 0.3 to 0.45 ml/g, more preferably from 0.33 to 0.4 ml/g, more preferably from 0.35 to 0.38 ml/g, and more preferably from 0.36 to 0.37 ml/g.

18. Process for the preparation of a catalyst comprising one or more alkaline earth metals selected from the group consisting of Mg, Ca, Sr, Ba, and combinations of two or more thereof, preferably of a catalyst according to any of embodiments 1 to 17, comprising
    (A) providing a zeolitic material having the CHA framework structure comprising $YO_2$ and $X_2O_3$, wherein Y is a tetravalent element and X is a trivalent element, wherein the framework of the zeolitic material contains substantially no phosphorous, and wherein the zeolitic material optionally comprises one or more alkaline earth metals;
    (B) mixing the zeolitic material provided in (A) with one or more metal oxides and/or metalloid oxides and with a solvent system;
    (C) optionally homogenizing the mixture obtained in (B);
    (D) molding of the mixture obtained in (B) or (C);
    (E) optional drying of the molding obtained in (D);
    (F) optional calcining of the molding obtained in (D) or (E);
    (G) optional impregnation of the molding obtained in (D), (E), or (F) with a solution containing one or more salts of the one or more alkaline earth metals;
    (H) optional drying of the molding obtained in (G); and
    (I) optional calcining of the molding obtained in (G) or (H);
    wherein the one or more alkaline earth metals in (A) and/or (G) are selected from the group consisting of Mg, Ca, Sr, Ba, and combinations of two or more thereof, preferably from the group consisting of Mg, Ca, Sr, and combinations of two or more thereof, wherein more preferably the one or more alkaline earth metals is Mg and/or Ca, preferably Mg.

19. The process of embodiment 18, wherein zeolitic material provided in (A) contains the one or more alkaline earth metals in an amount in the range of from 0.5 to 10 wt.-% calculated as the element and based on 100 wt.-% of the $YO_2$ in the zeolitic material, preferably from 1 to 8 wt.-%, more preferably from 2 to 7 wt.-%, more preferably from 3 to 6 wt.-%, more preferably from 3.5 to 5.5 wt.-%, more preferably from 4 to 5 wt.-%, more preferably from 4.3 to 4.9 wt.-%, and more preferably from 4.5 to 4.7 wt.-%.

20. The process of embodiment 18 or 19, wherein the one or more alkaline earth metals are contained in the zeolitic material provided in (A) as extra-framework ions.

21. The process of any of embodiments 18 to 20, wherein the zeolitic material provided in (A) contains substantially no phosphorous.

22. The process of any of embodiments 18 to 21, wherein Y is selected from the group consisting of Si, Sn, Ti, Zr, Ge, and mixtures of two or more thereof, Y preferably being Si.

23. The process of any of embodiments 18 to 22, wherein X is selected from the group consisting of Al, B, In, Ga, and mixtures of two or more thereof, X preferably being Al and/or B, and more preferably being Al.

24. The process of any of embodiments 18 to 23, wherein the zeolitic material provided in (A) displays a $YO_2:X_2O_3$ molar ratio in the range of from 5 to 100, preferably from 10 to 80, more preferably from 15 to 60, more preferably from 20 to 50, more preferably from 25 to 40, more preferably from 28 to 35, and more preferably from 30 to 32.

25. The process of any of embodiments 18 to 24, wherein the zeolitic material provided in (A) displays a specific surface area as determined according to DIN 66131 or ISO 9277:2010, preferably according to ISO 9277:2010, in the range of from 200 to 800 m²/g as determined according to DIN 66131, preferably from 300 to 750 m²/g, more preferably from 400 to 720 m²/g, more preferably from 450 to 700 m²/g, more preferably from 500 to 680 m²/g, more preferably from 550 to 650 m²/g, more preferably from 580 to 620 m²/g.

26. The process of any of embodiments 18 to 25, wherein the zeolitic material provided in (A) comprises one or more zeolites selected from the group consisting of (Ni (deta)$_2$)-UT-6, Chabazite, |Li-Na| [Al—Si—O]-CHA, DAF-5, Dehyd. Na-Chabazite, K-Chabazite, LZ-218, Linde D, Linde R, Phi, SSZ-62, UiO-21, Willhendersonite, ZK-14, ZYT-6, and combinations of two or more thereof, preferably from the group consisting of (Ni (deta)$_2$)-UT-6, Chabazite, |Li-Na| [Al—Si—O]-CHA, DAF-5, Dehyd. Na-Chabazite, K-Chabazite (Iran), LZ-218, Linde D, Linde R, Phi, SSZ-62, UiO-21, Willhendersonite, ZK-14, ZYT-6, and combinations of two or more thereof, and wherein even more preferably the zeolitic material comprises Chabazite.

27. The process of any of embodiments 18 to 26, wherein the solvent system comprises one or more solvents, wherein preferably the solvent system comprises one or more hydrophilic solvents, the hydrophilic solvents preferably being selected from the group consisting of polar solvents, more preferably from the group consisting of polar protic solvents, wherein more preferably the solvent system comprises one or more polar protic solvents selected from the group consisting of water, alcohols, carboxylic acids, and mixtures of two or more thereof, more preferably from the group consisting of water, C1-C5 alcohols, C1-C5 carboxylic acids, and mixtures of two or more thereof, more preferably from the group consisting of water, C1-C4 alcohols, C1-C4 carboxylic acids, and mixtures of two or more thereof, more preferably from the group consisting of water, C1-C3 alcohols, C1-C3 carboxylic acids, and mixtures of two or more thereof, more preferably from the group consisting of water, methanol, ethanol, propanol, formic acid, acetic acid, and mixtures of two or more thereof, more preferably from the group consisting of water, ethanol, acetic acid, and mixtures of two or more thereof, wherein more preferably the solvent system comprises water and/or ethanol, and wherein more preferably the solvent system comprises water, wherein even more preferably the solvent system consists of water.

28. The process of any of embodiments 18 to 27, wherein the one or more metal oxides and/or metalloid oxides in (B) are one or more metal oxides and/or metalloid oxides selected from the group of oxides of Mg, Y, La, Ti, Zr, Hf, Nb, Ta, Al, Ga, Si, and Ge, and mixtures and/or mixed oxides thereof, more preferably from the group consisting of oxides of La, Ti, Zr, Al, and Si, and mixtures and/or mixed oxides thereof, wherein more preferably the catalyst further comprises Al$_2$O$_3$ and/or SiO$_2$, preferably SiO$_2$.

29. The process of embodiment 28, wherein the one or more metal oxides and/or metalloid oxides are selected from the group consisting of silica, alumina, Mania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, and mixtures of two or more thereof, more preferably from the group consisting of fumed silica, colloidal silica, silica-alumina, colloidal silica-alumina, and mixtures of two or more thereof, more preferably from the group consisting of fumed silica, colloidal silica, and mixtures thereof, wherein more preferably the one or more metal oxides and/or metalloid oxides are fumed silica and/or colloidal silica, preferably colloidal silica. [colloidal silica]

30. The process of any of embodiments 18 to 29, wherein the mixture obtained in (B) displays a MO:zeolite weight ratio of the one or more metal oxides and/or metalloid oxides (MO) to the zeolitic material in the range of from 0.05 to 3 as calculated based on the weight of the calcined metal oxides and/or metalloid oxides and of the calcined zeolitic material, preferably in the range of from 0.1 to 2, more preferably from 0.15 to 1.5, more preferably from 0.2 to 1, more preferably from 0.25 to 0.8, more preferably from 0.3 to 0.6, more preferably from 0.35 to 0.55, more preferably from 0.38 to 0.5, more preferably from 0.4 to 0.46, and more preferably from 0.42 to 0.44.

31. The process of any of embodiments 18 to 30, wherein the mixture obtained in (B) displays a solvent system:zeolitic material weight ratio of the solvent system to the zeolitic material ranging from 0.5 to 2 as calculated based on the weight of the calcined zeolitic material, preferably in the range of from 0.8 to 1.7, more preferably from 1.0 to 1.5, more preferably from 1.1 to 1.4, and more preferably from 1.2 to 1.3.

32. The process of any of embodiments 18 to 31, wherein (B) further comprises mixing with one or more pore forming agents, wherein the one or more pore forming agents are preferably selected from the group consisting of polymers, carbohydrates, graphite, and mixtures of two or more thereof, more preferably from the group consisting of polymeric vinyl compounds, polyalkylene oxides, polyacrylates, polyolefins, polyamides, polyesters, cellulose and cellulose derivatives, sugars, and mixtures of two or more thereof, more preferably from the group consisting of polystyrene, C2-C3 polyalkylene oxides, cellulose derivatives, sugars, and mixtures of two or more thereof, more preferably from the group consisting of polystyrene, polyethylene oxide, C1-C2 hydroxyalkylated and/or C1-C2 alkylated cellulose derivatives, sugars, and mixtures of two or more thereof, more preferably from the group consisting of polystyrene, polyethylene oxide, hydroxyethyl methyl cellulose, and mixtures of two or more thereof, wherein more preferably the one or more pore forming agents consists of one or more selected from the group consisting of polystyrene, polyethylene oxide, hydroxyethyl methyl cellulose, and mixtures of two or more thereof, and wherein more preferably the one or more pore forming agents consists of hydroxyethyl methyl cellulose.

33. The process of any of embodiments 18 to 32, wherein the mixture obtained in (B) displays a pore forming agent: zeolitic material weight ratio of the one or more pore forming agents to the zeolitic material ranging from 0.001 to 0.3, as calculated based on the weight of the calcined zeolitic material, preferably in the range of from 0.005 to 0.2, more preferably from 0.01 to 0.15, more preferably from 0.02 to 0.12, more preferably from 0.03 to 0.09, more preferably from 0.035 to 0.07, more preferably from 0.04 to 0.06, and more preferably from 0.045 to 0.055.

34. The process of any of embodiments 18 to 33, wherein homogenizing of the mixture in (C) involves the kneading of the mixture obtained in (B).

35. The process of any of embodiments 18 to 34, wherein molding of the mixture in (D) involves extruding or spray granulating of the mixture obtained in (B) or (C), preferably extruding.

36. The process of any of embodiments 18 to 35, wherein the drying in (E) and/or (H) is effected at a temperature in the range from 50 to 220° C., preferably from 70 to 180° C., more preferably from 80 to 150° C., more preferably from 90 to 130° C., more preferably from 100 to 125° C., and more preferably from 110 to 120° C.

37. The process of any of embodiments 18 to 36, wherein the calcining of the molding in (F) and/or (I) is performed at a temperature ranging from 300 to 850° C., preferably from 350 to 750° C., more preferably from 400 to 700° C., more preferably from 450 to 650° C., more preferably from 475 to 600° C., and more preferably from 500 to 550° C.

38. The process of any of embodiments 18 to 37, wherein the solution used in (G) comprises one or more solvents selected from the group consisting of alcohols, water, mixtures of two or more alcohols, and mixtures of water and one or more alcohols, preferably from the group consisting of ($C_1$-$C_6$) alcohols, water, mixtures of two or more ($C_1$-$C_6$) alcohols, and mixtures of water and one or more ($C_1$-$C_6$) alcohols, more preferably ($C_1$-$C_4$) alcohols, water, mixtures of two or more ($C_1$-$C_4$) alcohols, and mixtures of water and one or more ($C_1$-$C_4$) alcohols, more preferably consisting of methanol, ethanol, n-propanol, isopropanol, water and mixtures of two or more thereof, more preferably consisting of methanol, ethanol, water and mixtures of two or more thereof, the solvent more preferably being water, preferably distilled water.

39. The process of any of embodiments 18 to 38, wherein the process further comprises
    (J) subjecting the molding obtained in (F) and/or (I), preferably (I) to a hydrothermal treatment;
    wherein preferably the hydrothermal treatment is conducted under autogenous pressure, wherein more preferably the hydrothermal treatment is conducted at a temperature ranging from 80 to 200° C., preferably from 90 to 180° C., more preferably from 100 to 170° C., more preferably from 110 to 160° C., and more preferably from 120 to 150° C.

40. The process of embodiment 39, wherein the hydrothermal treatment in (J) is performed with a water containing solvent system and/or with an aqueous solution, wherein preferably the hydrothermal treatment is performed with distilled water.

41. The process of embodiment 39 or 40, wherein the hydrothermal treatment in (J) is performed for a duration ranging from 1 to 48 hours, preferably from 2 to 36 hours, more preferably from 4 to 24 hours, more preferably from 5 to 12 hours, more preferably from 2 to 9 hours.

42. Catalyst obtainable and/or obtained according to the process of any of embodiments 18 to 41.

43. Method for the conversion of oxygenates to olefins comprising
    (i) providing a catalyst according to any of embodiments 1 to 17 and 42;
    (ii) providing a gas stream comprising one or more oxygenates;
    (iii) contacting the catalyst provided in (i) with the gas stream provided in (ii) and converting one or more oxygenates to one or more olefins.

44. The method of embodiment 43, wherein the gas stream provided in (ii) comprises one or more oxygenates selected from the group consisting of aliphatic alcohols, ethers, carbonyl compounds and mixtures of two or more thereof, preferably from the group consisting of ($C_1$-$C_6$) alcohols, di($C_1$-$C_3$)alkyl ethers, ($C_1$-$C_6$) aldehydes, ($C_2$-$C_6$) ketones and mixtures of two or more thereof, more preferably consisting of ($C_1$-$C_4$) alcohols, di($C_1$-$C_2$)alkyl ethers, ($C_1$-$C_4$) aldehydes, ($C_2$-$C_4$) ketones and mixtures of two or more thereof, more preferably from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, more preferably from the group consisting of methanol, ethanol, dimethyl ether, diethyl ether, ethyl methyl ether and mixtures of two or more thereof, the gas stream more preferably comprising methanol and/or dimethyl ether, and more preferably dimethyl ether.

45. The method of embodiment 43 or 44, wherein the content of oxygenates in the gas stream provided in (ii) is in the range from 2 to 100% by volume based on the total volume, preferably from 3 to 99% by volume, more preferably from 4 to 95% by volume, more preferably from 5 to 80% by volume, more preferably from 6 to 50% by volume, more preferably from 7 to 40% by volume, more preferably from 8 to 30% by volume, more preferably from 9 to 20% by volume, and more preferably from 10 to 15% by volume.

46. The method of any of embodiments 43 to 45, wherein the water content in the gas stream provided in (ii) is in the range from 5 to 60% by volume, preferably from 10 to 50% by volume, more preferably from 20 to 45% by volume, and more preferably from 30 to 40% by volume.

47. The method of any of embodiments 43 to 46, wherein the gas stream provided in (ii) further comprises one or more inert gases, preferably one or more inert gases in an amount ranging from 0.1 to 90% by volume, more preferably from 1 to 85% by volume, more preferably from 5 to 80% by volume, more preferably from 10 to 75% by volume, more preferably from 20 to 70% by volume, more preferably from 40 to 65% by volume, more preferably from 50 to 60% by volume.

48. The method of embodiment 47, wherein the one or more inert gases are selected from the group consisting of helium, neon, argon, krypton, nitrogen, carbon monoxide, carbon dioxide, and mixtures of two or more thereof, preferably from the group consisting of argon, nitrogen, carbon dioxide, and mixtures of two or more thereof, wherein more preferably the one or more inert gases comprise nitrogen, wherein more preferably the one or more inert gases is nitrogen.

49. The method of any of embodiments 43 to 48, wherein the contacting according to (iii) is effected at a temperature in the range from 200 to 700° C., preferably from 250 to 650° C., more preferably from 300 to 600° C., more preferably from 350 to 550° C., more preferably from 400 to 500° C., and more preferably from 425 to 475° C.

50. The method of any of embodiments 43 to 49, wherein the contacting according to (iii) is effected at a pressure in the range from 0.1 to 10 bar, preferably from 0.3 to 7 bar, more preferably from 0.5 to 5 bar, more preferably from 1 to 4.5 bar, more preferably from 1.3 to 4 bar, more preferably from 1.5 to 3.5 bar, more preferably from 1.8 to 3.3 bar, more preferably from 2.0 to 3.0 bar, more preferably from 2.2 to 2.8 bar, more preferably from 2.4 to 2.6 bar.

51. The method of any of embodiments 43 to 50, wherein the method is a continuous method, wherein the gas hourly space velocity (GHSV) in the contacting in (iii) is preferably in the range from 500 to 5,000 $h^{-1}$, preferably from 1,000 to 4,000 $h^{-1}$, more preferably from 1,500 to 3,500 h⁻¹, more preferably from 2,000 to 3,000 h⁻¹, more preferably from 2,200 to 2,800 h⁻¹ and more preferably from 2,400 to 2,600 h⁻¹.

52. Use of a catalyst according to any of embodiments 1 to 17 and 42 in the conversion of oxygenates to olefins, in a methanol-to-olefin process (MTO process), in a dimethylether to olefin process (DTO process), methanol-to-gasoline process (MTG process), in a methanol-to-hydrocarbon process, in a biomass to olefins and/or biomass to aromatics process, in a methane to benzene process, for alkylation of aromatics, or in a fluid catalytic cracking process (FCC process), preferably in a methanol-to-olefin process (MTO process) and/or in a dimethylether to olefin process (DTO process), and more preferably in a methanol-to-propylene process (MTP process), in a methanol-to-propylene/butylene process (MT3/4 process), in a dimethylether-to-propylene process (DTP process), in a dimethylether-to-propylene/butylene process (DT3/4 process), and/or in a di methylether-toethylene/propylene (DT2/3 process).

EXAMPLES

Figure 1:
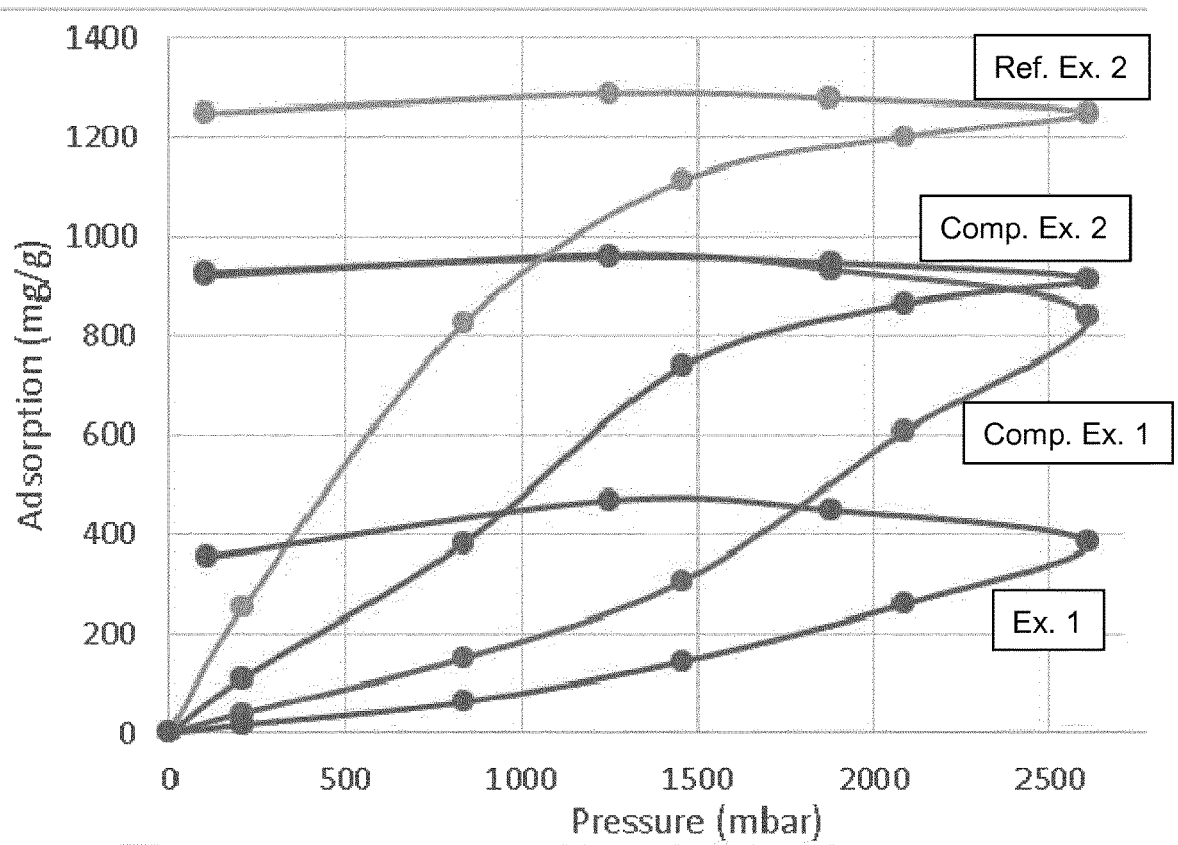
FIG. 1 shows the isobutene isotherms as obtained for the extrudates from Reference Example 2, Example 1, and Comparative Examples 1 and 2, respectively. In the figure, the pressure in mbar is shown along the abscissa and the absorption in mg/g are plotted along the ordinate.

Reference Example 1: Synthesis of Chabazite 2,040 kg of water were placed in a stirring vessel and 3,924 kg of a solution of 1-adamantyltrimethylammonium-hydroxide (20% aqueous solution) are added thereto under stirring. 415.6 kg of a solution of sodium hydroxide (20% aqueous solution) were then added, followed by 679 kg of aluminum triisopropylate (Dorox D 10, Ineos), after which the resulting mixture was stirred for 5 min. 7800.5 kg of a solution of colloidal silica (40% aqueous solution; Ludox AS 40, Sigma Aldrich) were then added and the resulting mixture stirred for 15 min before being transferred to an autoclave. 1,000 kg of distilled water used for washing out the stirring vessel were added to the mixture in the autoclave, and the final mixture was then heated under stirring for 19 h at 170° C. The solid product was then filtered off and the filter cake washed with distilled water. The resulting filter cake was then dispersed in distilled water in a spray dryer mix tank to obtain a slurry with a solids concentration of approximately 24% and the spray dried, wherein the inlet temperature was set to 477-482° C. and the outlet temperature was measured to be 127-129° C., thus affording a spray dried powder of SSZ-13 zeolite having the CHA framework structure.

The resulting material displayed a particle size distribution affording a D10 value of 1.4 μm, a D50 value of 5.0 μm, and a D90 value of 16.2 μm. The material displayed a surface area of 558 m²/g, a silica to alumina ratio of 34, a crystallinity of 105% as determined by powder X-ray diffraction. The sodium content of the product was determined to be 0.75 wt.-% calculated as $Na_2O$.

Reference Example 2: Molding of Chabazite from Reference Example 1

100 g of chabazite from reference example 1 was placed in a kneader, together with 5 g of hydroxyethyl methyl cellulose (Walocel), after which the components were kneaded for 5 min. 107.1 g of an aqueous solution of colloidal silica (40 wt.-%; Ludox AS 40) were then added and the mixture kneaded for 5 min. 45 g of distilled water were then continually added over a period of 40 min while kneading. The kneaded mass was then extruded to extrudates with a diameter of 2.5 mm. The extrudates thus obtained were dried for 4 h at 120° C. and subsequently heated under air at a rate of 2° C./min to 500° C. and calcined at that temperature for 5 h for obtaining 139.5 g of extrudates.

The extrudates displayed a BET surface area of 404 m²/g and a pore volume of 0.436 ml/g as obtained from mercury porosimetry. Elemental analysis of the extrudates afforded 1.8 wt.-% Al and 42 wt.-% Si.

Example 1: Impregnation of Molding of Reference Example 2 with Mg 65 g of extrudate from reference example 2 were placed in a 500 ml round bottom flask in a rotary evaporator. 20.5 g of $Mg(NO_3)_2 \times 6H_2O$ were dissolved in 12.4 g of water and the resulting solution sprayed via a glass injector directly onto the extrudate in the rotary evaporator within 10 min employing 100 norm liters of air during operation thereof. The impregnated extrudates were then subject to rotary evaporation a further 15 min and the extrudates subsequently removed from the rotary evaporator for drying in a convention drying cabinet at 80° C. for 4 h and subsequently at 120° C. for 4 h. The dried extrudates were then heated at 2° C./min to 500° C. under air and calcined at that temperature for 5 h for obtaining 68.2 g of the impregnated extrudates.

The extrudates displayed a BET surface area of 361 m²/g and a pore volume of 0.365 ml/g as obtained from mercury porosimetry. Elemental analysis of the extrudates afforded 1.6 wt.-% Al, 2.7 wt.-% Mg, and 38 wt.-% Si.

Comparative Example 1: Molding of Commercial SPAO-34

124 g of SAPO-34 (Zeolyst, Lot.-Nr. 2548-109) were placed in a kneader, together with 6.2 g of hydroxyethyl methyl cellulose (Walocel), after which the components were kneaded for 5 min. 133 g of an aqueous solution of colloidal silica (40 wt.-%; Ludox AS 40) were then added and the mixture kneaded for 5 min. 40 g of distilled water were then continually added over a period of 40 min while kneading. The kneaded mass was then extruded to extrudates with a diameter of 2.5 mm. The extrudates thus obtained were dried for 4 h at 120° C. and subsequently heated under air at a rate of 2° C./min to 500° C. and calcined at that temperature for 5 h for obtaining 186.14 g of extrudates.

The extrudates displayed a BET surface area of 389 m²/g and a pore volume of 0.3078 ml/g. Elemental analysis of the extrudates afforded 11.8 wt.-% Al and 16.2 wt.-% Si.

Comparative Example 2: Impregnation of Molding of Comparative Example 1 with Mg 60 g of extrudate from comparative example 1 were placed in a 500 ml round bottom flask in a rotary evaporator. 18.69 g of $Mg(NO_3)_2 \times 6H_2O$ were dissolved in 9.6 g of water and the resulting solution sprayed via a glass injector directly onto the extrudate in the rotary evaporator within 10 min employing 100 norm liters of air during operation thereof. The impregnated extrudates were then subject to rotary evaporation a further 15 min and the extrudates subsequently removed from the rotary evaporator for drying in a convention drying cabinet at 80° C. for 4 h and subsequently at 120° C. for 4 h. The dried extrudates were then heated at 2° C./min to 500° C. under air and calcined at that temperature for 5 h for obtaining 55.8 g of the impregnated extrudates.

The extrudates displayed a BET surface area of 282 m²/g and a pore volume of 0.331 ml/g. Elemental analysis of the extrudates afforded 12.9 wt.-% Al, 3.2 wt.-% Mg, and 17.4 wt.-% Si.

Example 2: Measurement of Isobutene Isotherms

The isobutene absorption isotherms of the extrudates obtained from Reference Example 2, Example 1, and Comparative Examples 1 and 2 were respectively measured. The results are displayed in FIG. 1. The adsorption isotherms were measured with isobutene, using a magnetic suspension balance from Rubotherm. The samples were filled in a sample container and activated for 4 h at 0.01 bar at 150° C., then the temperature was cooled to 80° C. The test gas was introduced step-by-step from 0.1 bar to 2.5 bar at 80° C. After the adsorption, the pressure was reduced in equivalent steps to desorb the sample. The software used to investigate the results was MessPro.

Example 3: Catalytic Testing for the Conversion of Dimethylether to Olefins (DTO)

Figure 2:
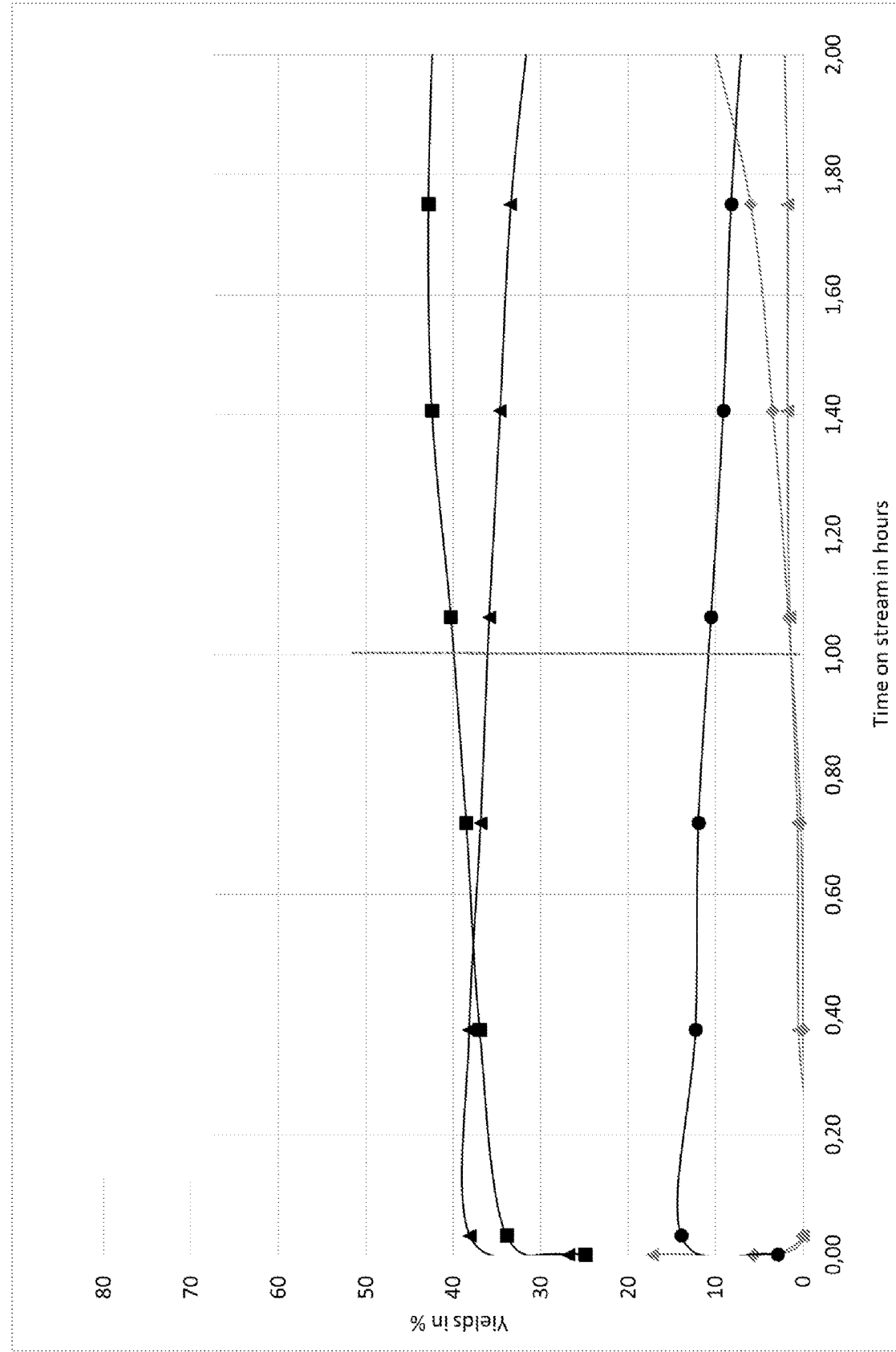
FIG. 2 shows the yields of methanol, dimethylether and C2-C4 olefins as obtained from the conversion of dimethylether to olefins using the extrudates from Example 1. In the figure, the time on stream in hours is shown along the abscissa and the yield of methanol "▲" and dimethylether "♦" in grey lines and the yield of $C_2H_4$ "■", $C_3H_6$ "▲" and $C_4H_8$ "●" in black lines are respectively plotted along the ordinate in %.

2.35 g of the extrudate from Example 1 (chabazite-containing extrudates impregnated with Mg) were loaded into a fixed bed reactor with an inner diameter of 15 mm. The fresh catalyst was exposed to multiple reaction/regeneration cycles. In the second reaction cycle the reaction temperature was set to 450° C. and the reactor pressure at the outlet to 2.5 bar. The gaseous hourly space velocity GHSV was 2500 1/h. The concentrations of the gases at the reactor inlet were $DME/H_2O/N_2$=10/35/55 Vol %. The catalyst was two hours on reaction stream. The yields of methanol, dimethylether and C2-C4 olefins are shown in FIG. 2 as a function of reaction time.

Figure 3:
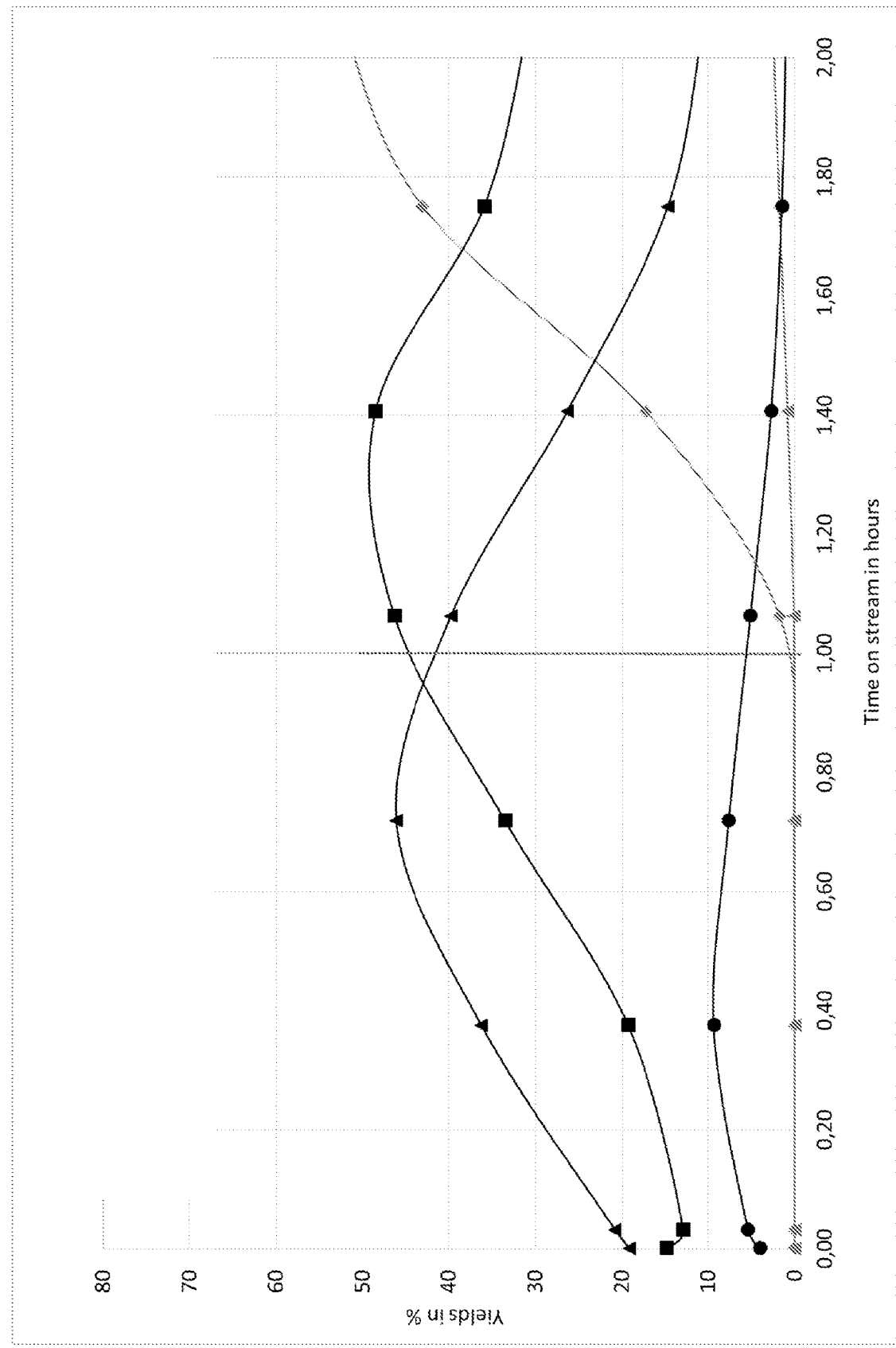
FIG. 3 shows the yields of methanol, dimethylether and $C_2$-$C_4$ olefins as obtained from the conversion of dimethylether to olefins using the extrudates from Reference Example 1. In the figure, the time on stream in hours is shown along the abscissa and the yield of methanol "▲" and dimethylether "♦" in grey lines and the yield of $C_2H_4$ "■", $C_3H_6$ "▲", and $C_4H_8$ "●" in black lines are respectively plotted along the ordinate in %.

The testing was repeated using 2.25 g of extrudate from Reference Example 1 (chabazite-containing extrudates). The yields of methanol, dimethylether and C2-C4 olefins are shown in FIG. 3 as a function of the reaction time.

Figure 4:
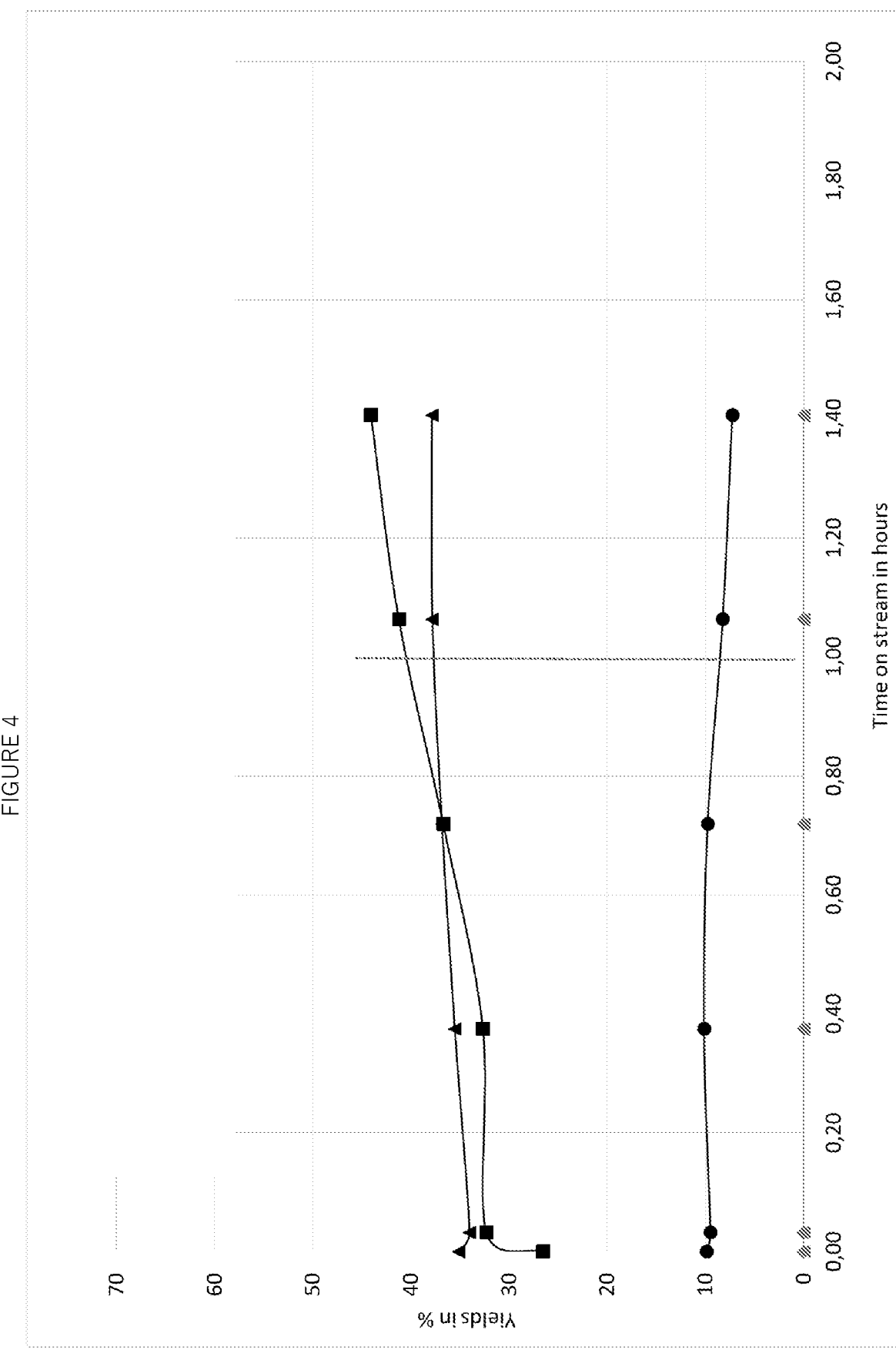
FIG. 4 shows the yields of methanol, dimethylether and $C_2$-$C_4$ olefins as obtained from the conversion of dimethylether to olefins using the extrudates from Comparative Example 1. In the figure, the time on stream in hours is shown along the abscissa and the yield of methanol "▲" and dimethylether "♦" in grey lines and the yield of $C_2H_4$ "■", $C_3H_6$ "▲", and $C_4H_8$ "●" in black lines are respectively plotted along the ordinate in %.

The testing was repeated using 2.72 g of extrudate from Comparative Example 1 (SAPO-34-containing extrudates). The yields of methanol, dimethylether and C2-C4 olefins are shown in FIG. 4 as a function of the reaction time.

Figure 5:
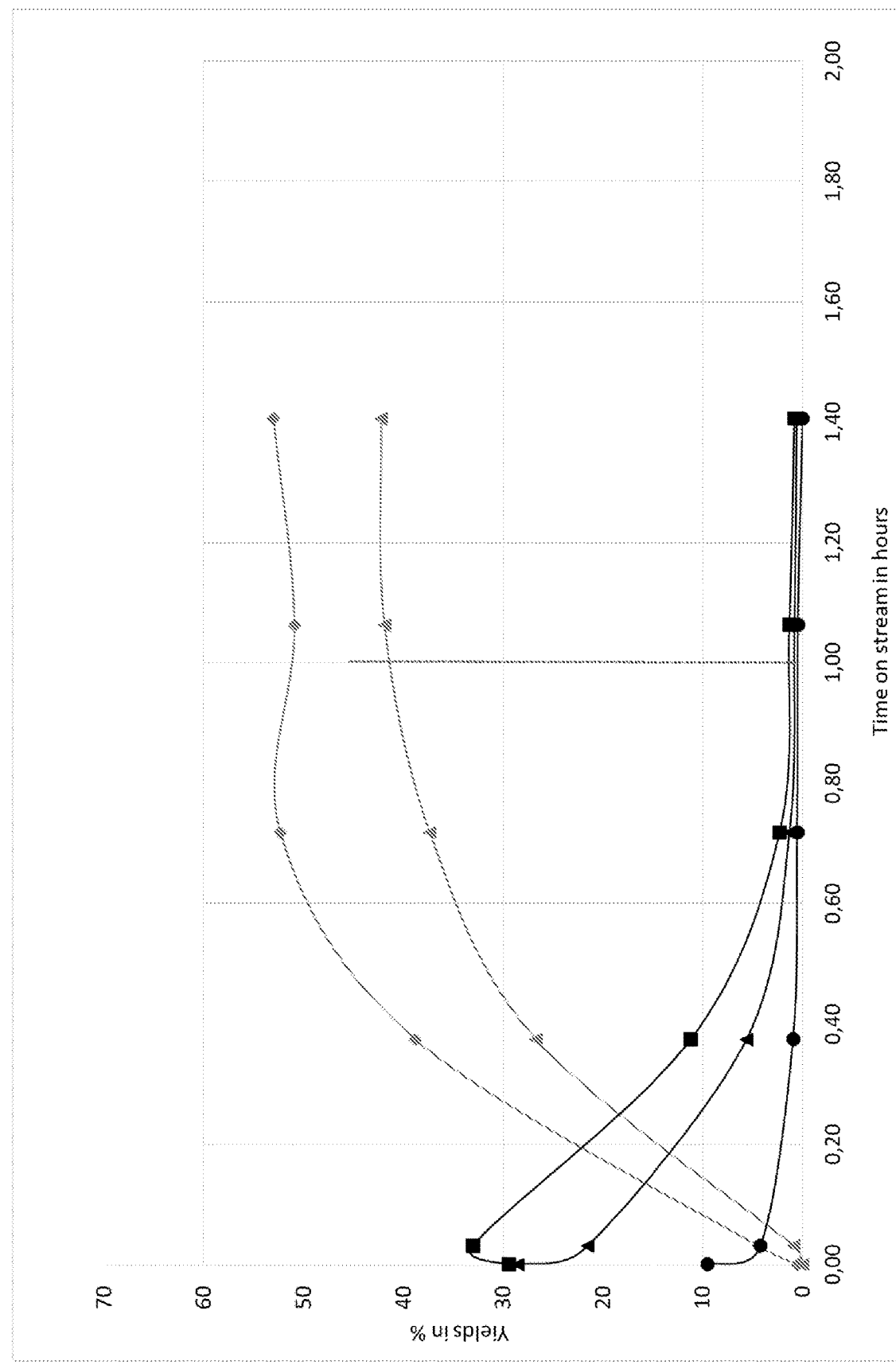
FIG. 5 shows the yields of methanol, dimethylether and $C_2$-$C_4$ olefins as obtained from the conversion of dimethylether to olefins using the extrudates from Comparative Example 2. In the figure, the time on stream in hours is shown along the abscissa and the yield of methanol "▲" and dimethylether "♦" in grey lines and the yield of $C_2H_4$ "■", $C_3H_6$ "▲", and $C_4H_8$ "●" in black lines are respectively plotted along the ordinate in %.

The testing was finally repeated using 2.57 g of extrudate from Comparative Example 2 (chabazite-containing extrudates impregnated with Mg). The yields of methanol, dimethylether and C2-C4 olefins are shown in FIG. 5 as a function of the reaction time.

As may be taken from the results displayed in FIGS. 2-5 it has surprisingly been found that the impregnation of extrudates respectively containing chabazite and SAPO-34 with Mg leads to completely different results. Thus, as may be taken from FIGS. 3 and 4 displaying the nonimpregnated extrudates, SAPO-34 (see FIG. 4) displays a relatively high yield in ethylene and propylene and a lower yield in butylene, wherein the yield in ethylene increases and the yield in butylene gradually decreases during the time on stream. Chabazite (see FIG. 3), on the other hand, displays high yields in ethylene and propylene and a lower yield in butylene as well, wherein the extrudates however display high variations in yield and only poor catalyst lifetime compared to the SAPO-34 extrudates. Impregnation of the SAPO-34 extrudates with Mg (see FIG. 5) leads to a rapid deactivation of the catalyst, such that it may find no application among the known SAPO-34 catalysts. Quite unexpectedly, however, the impregnation of chabazite containing extrudates with Mg (see FIG. 2) leads to a considerable improvement of both the catalyst lifetime, as well as with respect to the constance of the product distribution pattern. In particular, impregnation of the chabazite extrudates with Mg not only leads to a high and constant level of the yields in ethylene and propylene comparable to those obtained with the SAPO-34 extrudates, but further leads to a yield in butylene which exceeds those obtained with the latter in function of the time on stream of the respective catalyst.

Thus, it has quite surprisingly been found that chabazite loaded with Mg affords a highly efficient and durable catalyst for the conversion of dimethylether to C2-C4 olefins, wherein the inventive catalyst even outperforms the SAPO-34 catalysts known in the art, in particular with respect to the yield in butylene. Said results are highly unexpected, in particular considering the poor performance of the chabazite extrudates and furthermore considering the highly detrimental effect of Mg-impregnation on SAPO-34 extrudates. Consequently, the skilled person would by no means have expected that results achieved by the present invention.

LIST OF PRIOR ART REFERENCES CITED IN THE APPLICATION

Applied Catalysis 1988, Vol. 40, No. 1-2, p. 316
Applied Catalysis 1990, vol. 64, pp. 31-40, 1990

U.S. Pat. No. 8,148,587
U.S. Pat. No. 6,448,197
US 20040048734
CN 1441701A
WO 0162382
WO 0160746
U.S. Pat. No. 6,005,155
U.S. Pat. No. 5,932,512
U.S. Pat. No. 6,051,746
WO 9829370
U.S. Pat. No. 5,925,586
U.S. Pat. No. 6,040,264
U.S. Pat. No. 5,962,762
U.S. Pat. No. 5,912,393
U.S. Pat. No. 5,126,308
U.S. Pat. No. 5,095,163
U.S. Pat. No. 6,046,371
U.S. Pat. No. 6,051,745
EP 418142
U.S. Pat. No. 7,078,364
Zhang, J. in Microporous and Mesoporous Materials 2008, 111, pp. 478-487
Ji, Y. et al. in ACS Catalysis 2015, 5, pp. 4456-4465
Yarulina, I. et al. in Catal. Sci. Technol. 2016, 6, 2663-2678
Itakura, M et al. in Microporous and Mesoporous Materials 2011, 144, 91-96

The invention claimed is:

1. A catalyst comprising
one or more metal oxides and/or metalloid oxides and
a zeolitic material having the CHA framework structure comprising $YO_2$ and $X_2O_3$,
wherein Y is Si and X is Al, wherein the zeolitic material comprises Mg and wherein the framework of the zeolitic material comprised in the catalyst contains substantially no phosphorous; wherein the one or more metal oxides and/or metalloid oxides comprises, $Al_2O_3$ and/or $SiO_2$ and wherein the zeolitic material comprised in the catalyst contains Mg in an amount in the range of from 2 to 7 wt. % calculated as the element and based on 100 wt. % of the $YO_2$ in the zeolitic material and wherein the zeolitic material contains substantially no phosphorous and
wherein the catalyst is in the form of a shaped body in the form of granulates and/or extrudates.

2. The catalyst of claim 1, wherein the zeolite material and the metal oxide and/or metalloid oxide is calcined and the catalyst displays a MO:zeolite weight ratio of the one or more metal oxides and/or metalloid oxides (MO) to the zeolitic material in the range of from 0.05 to 3 as calculated based on the weight of the calcined metal oxides and/or metalloid oxides and of the calcinated zeolitic material.

3. A process for the preparation of the catalyst as claimed in claim 1, comprising $YO_2$ and $X_2O_3$, wherein Y is Si and X is Al,
(B) mixing the zeolitic material provided in claim 1 with one or more metal oxides and/or metalloid oxides and with a solvent system;
(C) optionally homogenizing the mixture obtained in (B);
(D) molding of the mixture obtained in (B) or (C);
(E) optional drying of the molding obtained in (D);
(F) optional calcining of the molding obtained in (D) or (E);
(G) impregnation of the molding obtained in (D), (E), or (F) with a solution containing one or more salts of Mg;
(H) optional drying of the molding obtained in (G); and
(I) optional calcining of the molding obtained in (G) or (H).

4. A catalyst comprising Mg obtained according to the process of claim 3.

5. A method for the conversion of oxygenates to olefins comprising
(i) providing the catalyst according to claim 1;
(ii) providing a gas stream comprising one or more oxygenates;
(iii) contacting the catalyst provided in (i) with the gas stream provided in (ii) and converting one or more oxygenates to one or more olefins.

6. The method of claim 5, wherein the gas stream provided in (ii) comprises one or more oxygenates selected from the group consisting of aliphatic alcohols, ethers, carbonyl compounds and mixtures of two or more thereof.

7. The method of claim 5, wherein the water content in the gas stream provided in (ii) is in the range from 5 to 60% by volume.

8. The method of claim 5, wherein the contacting according to (iii) is effected at a temperature in the range from 200 to 700° C.

9. A process comprising:
(i) preparing the catalyst according to claim 1,
(ii) providing the catalyst of step (i) to a process selected from the group consisting of
conversion of oxygenates to olefins,
a methanol-to-olefin process (MTO process),
a dimethylether to olefin process (DTO process),
methanol-to-gasoline process (MTG process),
a methanol-to-hydrocarbon process,
a biomass to olefins and/or biomass to aromatics process,
a methane to benzene process, and
for alkylation of aromatics.

10. The catalyst of claim 1, wherein the catalyst comprises a composite of the zeolitic material and the one or more metalloid oxides.

11. The catalyst of claim 1, wherein the one or more metal oxides and/or metalloid oxides comprises $Al_2O_3$.

12. The catalyst of claim 1, wherein the one or more metal oxides and/or metalloid oxides comprises $SiO_2$.

13. The catalyst of claim 1, wherein the one or more metal oxides and/or metalloid oxides comprises $Al_2O_3$ and $SiO_2$.

14. The catalyst of claim 1, wherein the catalyst contains Mg in an amount in the range of from 3.5 to 5.5 wt. % calculated as the element and based on 100 wt. % of the $YO_2$.

15. The catalyst of claim 1, wherein the catalyst contains Mg in an amount in the range of from 4.3 to 4.9 wt. % calculated as the element and based on 100 wt. % of the $YO_2$.

16. The catalyst of claim 1, wherein the Mg is present in the catalyst as extra-framework ions.

17. The catalyst of claim 1, wherein the specific surface area of the catalyst is in the range of from 250 to 500 $m^2/g$.

18. The catalyst of claim 1, wherein the specific pore volume of the catalyst is in the range of from 0.2 to 0.5 ml/g.

19. The catalyst of claim 1, wherein
the specific surface area of the catalyst is in the range of from 350 to 375 $m^2/g$,
the specific pore volume of the catalyst is in the range of from 0.36 to 0.37 ml/g and
the catalyst is in the form of a shaped body in the form of extrudates.

* * * * *